United States Patent
Nomura et al.

(10) Patent No.: US 10,486,134 B2
(45) Date of Patent: Nov. 26, 2019

(54) POROUS COORDINATION POLYMER AND GAS STORAGE USING THE SAME

(71) Applicant: Panasonic Intellectual Property Management Co., Ltd., Osaka (JP)

(72) Inventors: Takaiki Nomura, Osaka (JP); Hideki Hata, Osaka (JP); Motomasa Yonezumi, Osaka (JP); Kazuhito Hato, Osaka (JP); Atsuo Okaichi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 184 days.

(21) Appl. No.: 15/662,635

(22) Filed: Jul. 28, 2017

(65) Prior Publication Data
US 2018/0093251 A1    Apr. 5, 2018

(30) Foreign Application Priority Data

Oct. 3, 2016  (JP) .................................. 2016-196010
Oct. 3, 2016  (JP) .................................. 2016-196011
Oct. 3, 2016  (JP) .................................. 2016-196012

(51) Int. Cl.
| | | |
|---|---|---|
| *B01J 20/26* | (2006.01) | |
| *B01J 20/22* | (2006.01) | |
| *B01J 20/30* | (2006.01) | |
| *C01B 3/00* | (2006.01) | |
| *C08G 79/00* | (2006.01) | |
| *F17C 11/00* | (2006.01) | |

(52) U.S. Cl.
CPC ......... *B01J 20/226* (2013.01); *B01J 20/3071* (2013.01); *B01J 20/3078* (2013.01); *B01J 20/3085* (2013.01); *C01B 3/0015* (2013.01); *C08G 79/00* (2013.01); *F17C 11/005* (2013.01); *F17C 2221/012* (2013.01)

(58) Field of Classification Search
CPC .. B01J 20/0244; B01J 20/226; B01J 20/3071; B01J 20/3078; C07F 3/06; Y02E 60/321; Y02E 60/324
See application file for complete search history.

(56) References Cited

U.S. PATENT DOCUMENTS

| | | | |
|---|---|---|---|
| 6,929,679 B2 | 8/2005 | Müller et al. | |
| 9,675,958 B2 * | 6/2017 | Kang ..................... | B01J 20/226 |

FOREIGN PATENT DOCUMENTS

| | | |
|---|---|---|
| JP | 2005-525218 | 8/2005 |
| JP | 2010-209042 | 9/2010 |

OTHER PUBLICATIONS

Antek G. Wong-Foy et al., "Exceptional H2 Saturation Uptake in Microporous Metal-Organic Frameworks", Journal of American Chemical Society, 2006, 128, pp. 3494-3495, Mar. 1, 2006.

(Continued)

*Primary Examiner* — Sanza L. McClendon
(74) *Attorney, Agent, or Firm* — McDermott Will & Emery LLP

(57) ABSTRACT

The present invention provides a porous coordination polymer having high ability of storing a gas. The porous coordination polymer according to the present invention comprises zinc cluster ions and one kind of tricarboxylic acid ions selected from the group consisting of the following chemical formula (I), the following chemical formula (II), and the following chemical formula (III);

[Chem. 1]

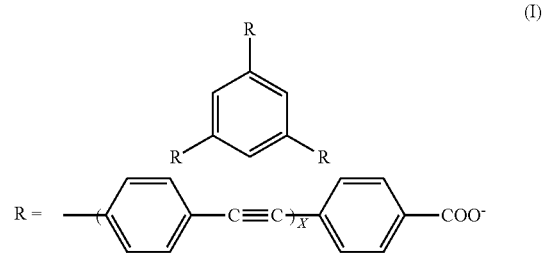

[Chem. 2]

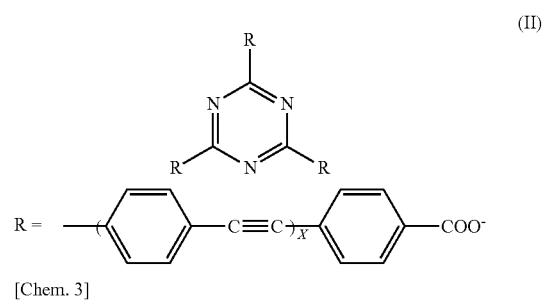

[Chem. 3]

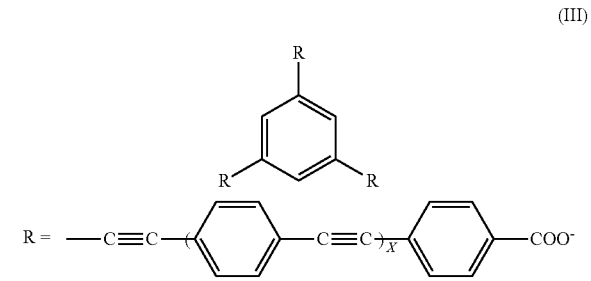

where X represents a natural number of not less than 1 and not more than 3, wherein the tricarboxylic acid ions are bound to the zinc cluster ions as terdentate ligands.

13 Claims, 25 Drawing Sheets

(56) References Cited

OTHER PUBLICATIONS

Daqiang Yuan et al., "An Isoreticular Series of Metal-Organic Frameworks with Dendritic Hexacarboxylate Ligands and Exceptionally High Gas-Uptake Capacity", Angewandte Chemie International Edition, 2010, vol. 49, 5357-5361, Jun. 11, 2010.
Dipendu Saha et al., "Structural Stability of Metal Organic Framework MOF-177", Journal of Physics Chemical Letters, 2010, 1(1), pp. 73-78, Nov. 6, 2009.
The Extended European Search Report dated Jan. 31, 2018 for the related European Patent Application No. 171837263.
Ding Lifeng et al: "Hydrogen and methane storage in ultrahigh surface area Metal-Organic Frameworks", Microporous and Mesoporous Materials, vol. 182, Jan. 8, 2013 (Jan. 8, 2013), pp. 185-190, XP028739366.
H. Furukawa et al: "Ultrahigh Porosity in Metal-Organic Frameworks", Science, vol. 329, No. 5990, Jul. 23, 2010 (Jul. 23, 2010), pp. 424-428, XP055439863.
Qingxia Yao et al: "Series of Highly Stable Isoreticular Lanthanide Metal-Organic Frameworks with Expanding Pore Size and Tunable Luminescent Properties", Chemistry of Materials, vol. 27, No. 15, Jul. 23, 2015 (Jul. 23, 2015), pp. 5332-5339, XP055439741.

\* cited by examiner

MOF-177 Structure $r_{BTB}$ = 0.863 nanometers $r_{MOF-177}$ = 1.06 nanometers

POROUS COORDINATION POLYMER AND GAS STORAGE USING THE SAME

BACKGROUND

1. Technical Field

The present disclosure relates to a porous coordination polymer. Furthermore, the present disclosure relates to a method for storing a gas using the porous coordination polymer and a gas storage device comprising the porous coordination polymer.

2. Description of the Related Art

A porous coordination polymer is composed of (i) metal ions or metal cluster ions and (ii) organic compounds each having two or more functional groups capable of binding to the metal ions or the metal cluster ions as ligands. Hereinafter, such an organic compound is referred to as "multidentate ligand". The porous coordination polymer has ability of storing a gas. As is disclosed in U.S. Pat. No. 6,929,679, a pore size and a surface area of the porous coordination polymer may be changed variously depending on the multidentate ligand. An amount of the gas stored in the porous coordination polymer can be increased by proper selection of the metal ions (or metal cluster ions) and the multidentate ligands, as disclosed in JP 2010-209042A, Antek G. Wong-Foy et al., "Exceptional $H_2$ Saturation Uptake in Microporous Metal-Organic Frameworks", Journal of American Chemical Society, 2006, 128, 3494-3495, and Daqiang Yuan, et al., "An Isoreticular Series of Metal-Organic Frameworks with Dendritic Hexacarboxylate Ligands and Exceptionally High Gas-UptakeCapacity", Angewandte Chemie International Edition, 2010, Vol. 49, 5357-5361.

SUMMARY

The present invention provides a porous coordination polymer comprising:

zinc cluster ions; and one kind of tricarboxylic acid ions selected from the group consisting of the following chemical formula (I), the following chemical formula (II), and the following chemical formula (III);

[Chem. 1]

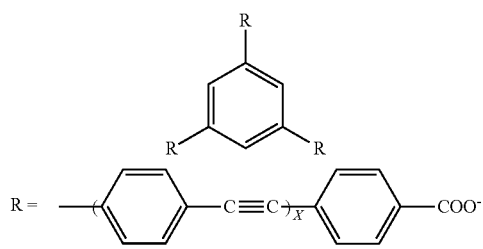

(I)

[Chem. 2]

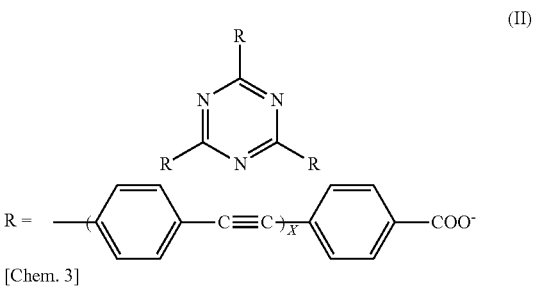

(II)

[Chem. 3]

(III)

where X represents a natural number of not less than 1 and not more than 3, wherein the tricarboxylic acid ions are bound to the zinc cluster ions as terdentate ligands.

The present invention includes a gas storage device comprising the porous coordination polymer.

The present disclosure provides a porous coordination polymer having high ability of storing a gas.

DETAILED DESCRIPTION OF THE EMBODIMENT

Embodiment

Hereinafter, an embodiment of the present disclosure will be described with reference to the drawings.

Figure 1:
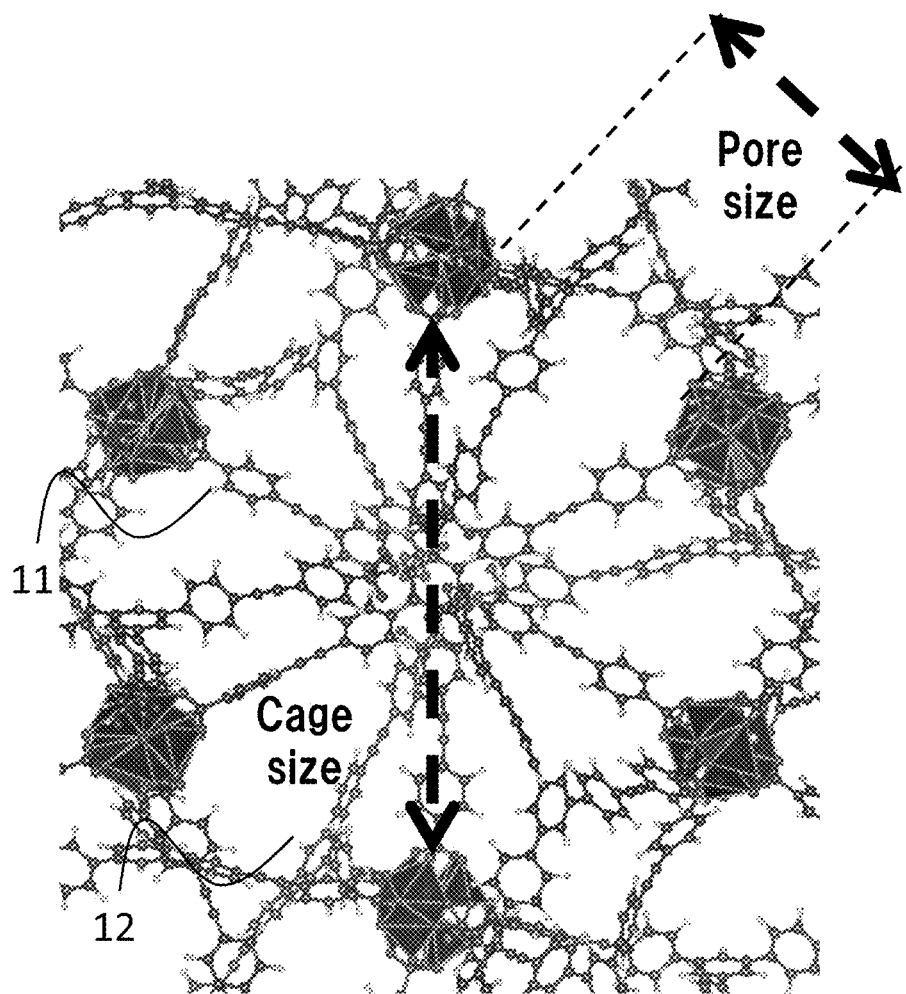
FIG. 1 shows a schematic view of the porous coordination polymer according to an embodiment.

As shown in FIG. 1, the porous coordination polymer 1 according to the present embodiment is composed of zinc cluster ions 11 and terdentate ligands 12. The porous coordination polymer 1 according to the present embodiment is formed two-dimensionally or three-dimensionally of the zinc cluster ions 11 and the terdentate ligands 12.

Each of the terdentate ligands 12 is a compound having three functional groups each capable of binding to the zinc cluster ion 11. Each of the terdentate ligands 12 is formed of a tricarboxylic acid ion selected from the group consisting of the following chemical formulas (I)-(III).

[Chem. 1]

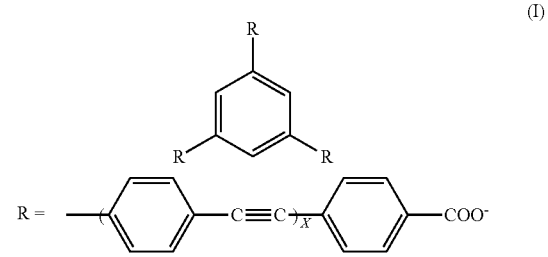

(I)

[Chem. 2]

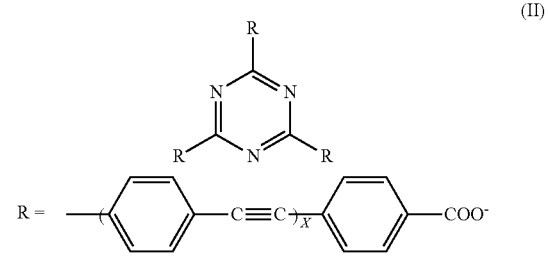

(II)

[Chem. 3]

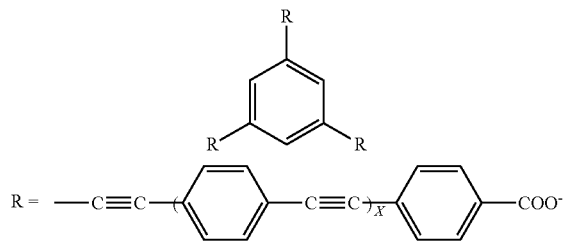

(III)

where X represents a natural number of not less than 1 and not more than 3.

Each of the zinc cluster ions 11 has high gas affinity. An example of the zinc cluster ion 11 is a $Zn_4O^{6+}$ cluster. The $Zn_4O^{6+}$ cluster is formed of plural $Zn_4O^{6+}$ molecules. The terdentate ligands 12 decide the pore size and the cage size of the porous coordination polymer. For more detail of the pore size and the cage size of the porous coordination polymer 1, see FIG. 1. As the pore size is larger, a gas enters the porous coordination polymer 1 more easily. As the cage size is larger, the gas is stored more easily in the porous coordination polymer 1. The porous coordination polymer 1 according to the present embodiment has high ability of storing a gas. As one example, the porous coordination polymer 1 according to the present embodiment has higher gas storage ability than a known porous coordination polymer MOF-177. Please note that the porous coordination polymer MOF-177 is composed of the $Zn_4O^{6+}$ cluster ions and the tricarboxylic acid ions represented by the chemical formula (I) in which the value of x is equal to 0 (more exactly, trivalent anion of 1,3,5-tris(4-carboxyphenyl) benzene (CAS No. 50446-44-1), which has the following chemical formula (IV)).

[Chem. 4]

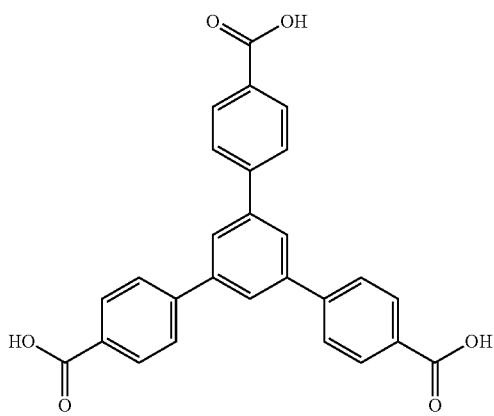

(IV)

As described in more detail in the inventive example later, the present inventors believe that the porous coordination polymer 1 according to the present embodiment has the same structure as the porous coordination polymer MOF-177. For this reason, in the X-ray diffraction spectrum of the porous coordination polymer 1 according to the present embodiment, peaks appear in the range of 2θ of not less than 3 and not more than 11.

Since the porous coordination polymer 1 according to the present embodiment has different terdentate ligands 12 from the porous coordination polymer MOF-177, the porous coordination polymer 1 according to the present embodiment has significantly higher gas-storing ability than the porous coordination polymer MOF-177. The terdentate ligands 12 contained in the porous coordination polymer 1 according to the present embodiment has a larger structure than the ligands contained in the porous coordination polymer MOF-177. In other words, as is clear from the chemical formulas (I)-(IV), the distance between the aryl group (or the $C_3N_3$ group in the chemical formula (II)) located at the center of the terdentate ligand 12 included in the porous coordination polymer 1 according to the present embodiment and the carboxylate ion located at the end of the terdentate ligand 12 is longer than that of the porous coordination polymer MOF-177. Therefore, the pore size and the cage size of the porous coordination polymer 1 are increased. Furthermore, unlike the porous coordination polymer MOF-177, since the terdentate ligands 12 contained in the porous coordination polymer 1 according to the present embodiment contains a carbon-carbon triple bond, the terdentate ligands 12 included in the porous coordination polymer 1 according to the present embodiment has a larger pi electron cloud than the porous coordination polymer MOF-177. Such a large pi electron cloud improves gas-storing ability significantly. Particularly, note that a hydrogen molecule is drawn to the large pi electron cloud easily.

Since the carboxylic acid ion represented by the chemical formula (II) has a six-membered ring unsaturated structure containing three nitrogen atoms (i.e., triazine structure), the carboxylic acid ion represented by the chemical formula (II) has a larger polarization than the carboxylic acid ion represented by the chemical formula (I) or the chemical formula (III). Therefore, the carboxylic acid ion represented by the chemical formula (II) has higher gas-storing ability than the carboxylic acid ion represented by the chemical formula (I) or the chemical formula (III).

The value of X is not less than 1 and not more than 3. It would be difficult to find a solvent suitable for synthesis of the tricarboxylic acid ion having a value of X of not less than 4. The reason will be described now. Since the zinc cluster ions 11 are cations, the solvent capable of dissolving the zinc cluster ions 11 is hydrophilic. On the other hand, since the tricarboxylic acid having a value of X of not less than 4 has a strong hydrophobicity derived from four or more aryl groups and four or more acetylene groups, the solvent capable of dissolving the carboxylic acid having a value of X of not less than 4 is hydrophobic. Note that the contribution to the hydrophilicity by the three carboxyl groups included in the tricarboxylic acid having a value of X of not less than 4 is smaller than the contribution to the hydrophobicity by the four or more aryl groups and the four or more acetylene groups. From the viewpoint of these two contradicting solubility, it would be difficult to find a solvent suitable for the synthesis of the tricarboxylic acid ion having a value of X of not less than 4. Therefore, the value of X is not less than 1 and not more than 3.

In a case where the value of X is equal to 1 in the chemical formula (I), the terdentate ligand 12 is a tricarboxylic acid ion having the following structure (hereinafter, referred to as "ligand A1"). Hereinafter, the porous coordination polymer 1 including the ligand A1 is referred to as "PMOF-1".

[Chem. 5]
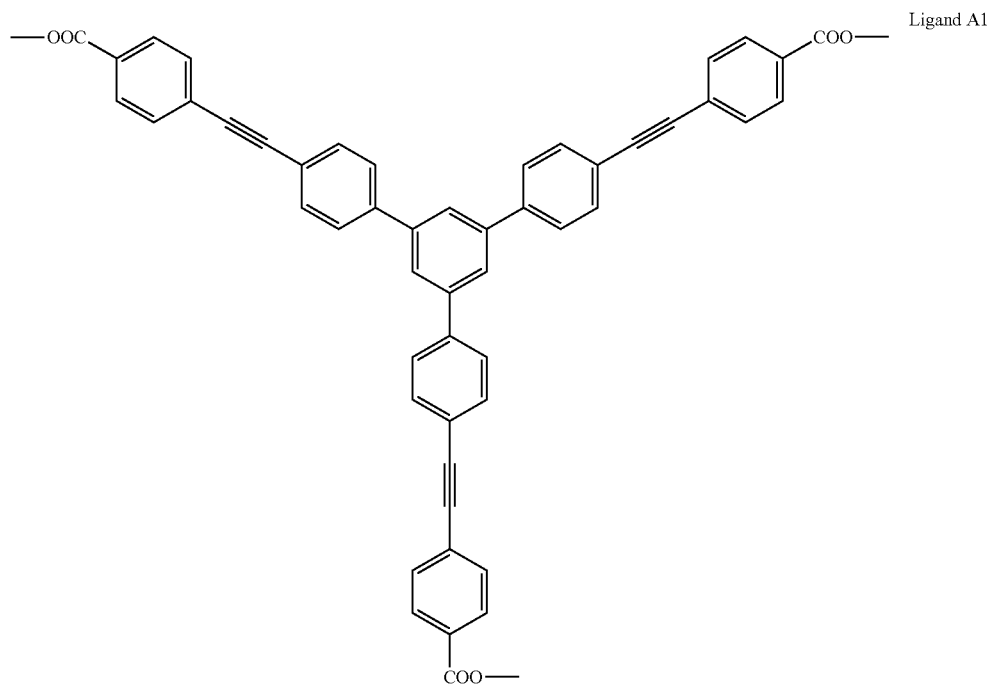
Ligand A1
In a case where the value of X is equal to 2 in the chemical formula (I), the terdentate ligand 12 is a tricarboxylic acid ion having the following structure (hereinafter, referred to as "ligand A2"). Hereinafter, the porous coordination polymer 1 including the ligand A2 is referred to as "PMOF-5".
[Chem. 6]
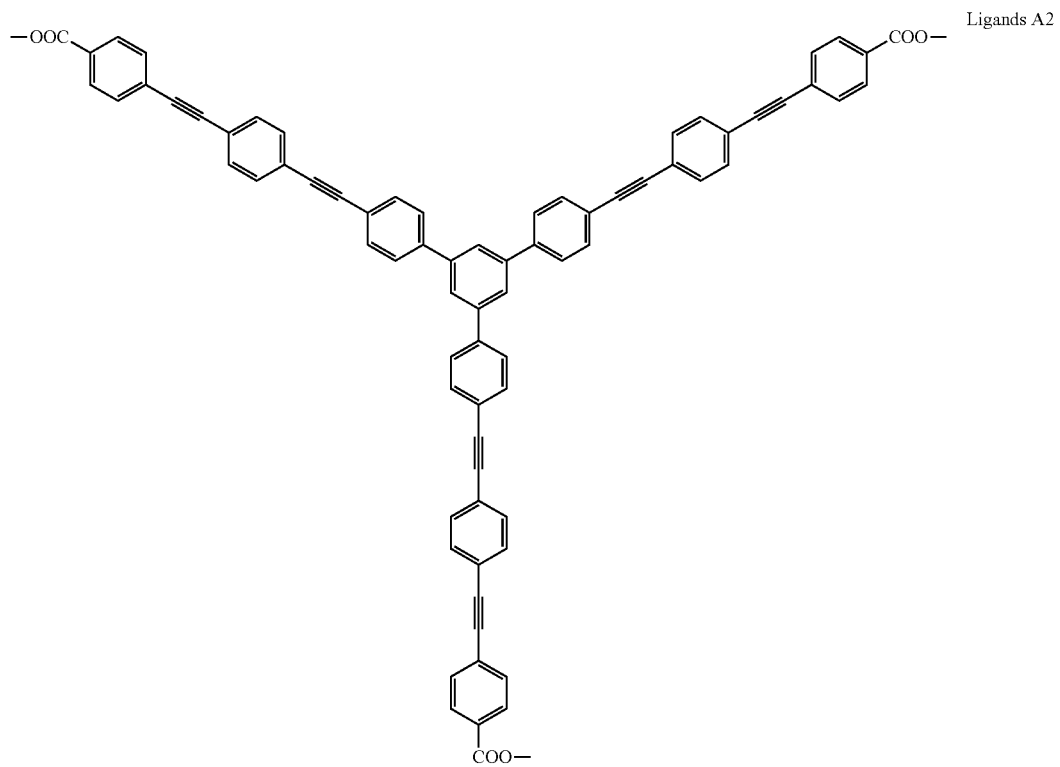
Ligands A2

In a case where the value of X is equal to 1 in the chemical formula (II), the terdentate ligand 12 is a tricarboxylic acid ion having the following structure (hereinafter, referred to as "ligand B"). Hereinafter, the porous coordination polymer 1 including the ligand B is referred to as "PMOF-1N".

The porous coordination polymer 1 may be synthesized in the following method. First, a N,N-dimethylformamide solution containing zinc nitrate tetrahydrate and a tricarboxylic acid having the following structure (hereinafter, referred to as "starting material A1, A2, B, or C") is prepared. The

[Chem. 7]

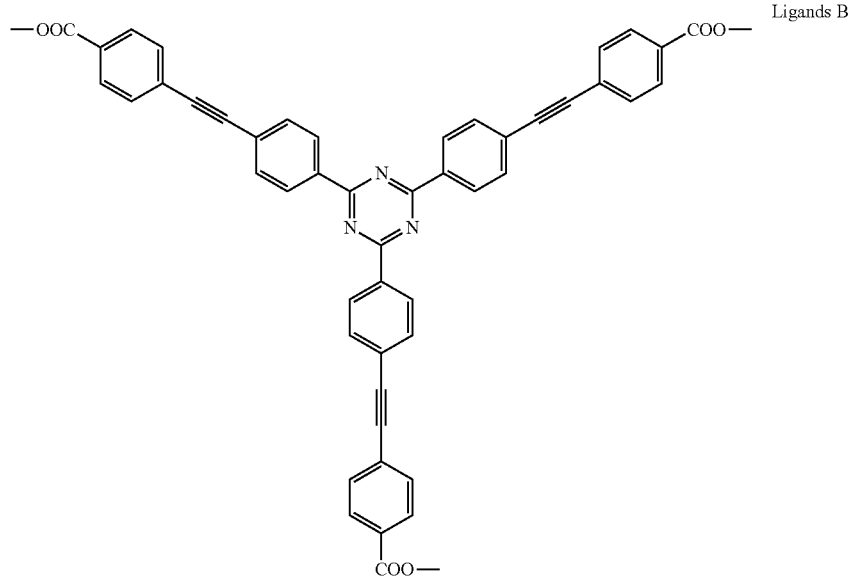

Ligands B

In a case where the value of X is equal to 1 in the chemical formula (III), the terdentate ligand 12 is a tricarboxylic acid ion having the following structure (hereinafter, referred to as "ligand C"). Hereinafter, the porous coordination polymer 1 including the ligand C is referred to as "PMOF-3".

starting materials A1, A2, B and C correspond to the tricarboxylic acid ions of the ligands A1, A2, B and C, respectively. Then, the N,N-dimethylformamide solution is heated. As one example, the heating temperature is 100 degrees Celsius and the heating time is 72 hours. In the

[Chem. 8]

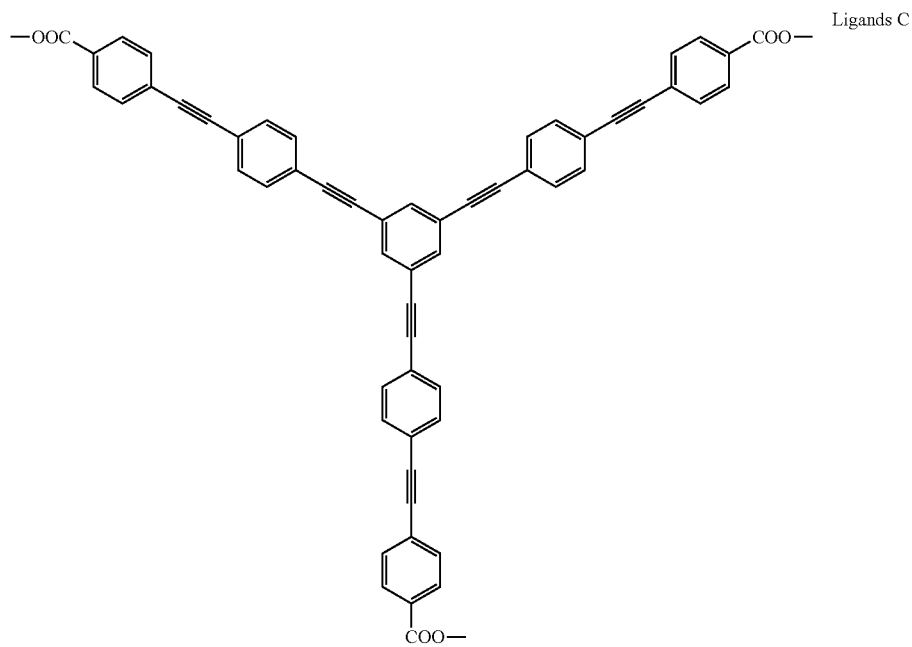

Ligands C

N,N-dimethylformamide solution, the $Zn_4O^{6+}$ clusters are formed first. Then, the carboxyl group ion of the tricarboxylic acid ion included in the ligand A1, A2, B, and C is bound to the $Zn_4O^{6+}$ cluster. In other words, a coordination bond is formed between the carboxyl group ion and the $Zn_4O^{6+}$ cluster. This coordinate bond is repeated. In this way, a polymer is formed three-dimensionally. As a result, a porous coordination polymer is precipitated in the N,N-dimethylformamide solution. The porous coordination polymer is centrifuged from the N,N-dimethylformamide solution. Then, the porous coordination polymer is washed using N,N-dimethylformamide, methanol, and dichloromethane in this order. Finally, the washed porous coordination polymer is dried. In this way, a porous coordination polymer is provided.

[Chem. 9]

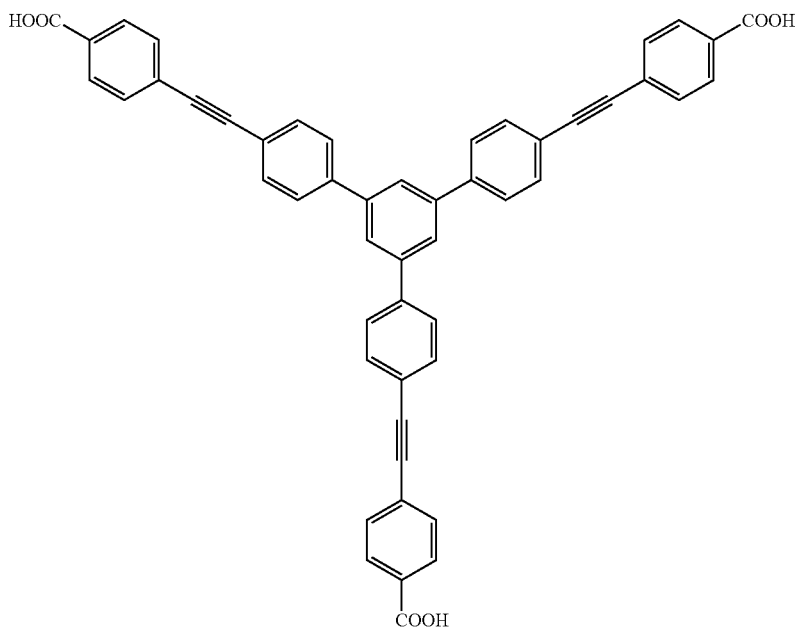

Starting material A1

[Chem. 10]

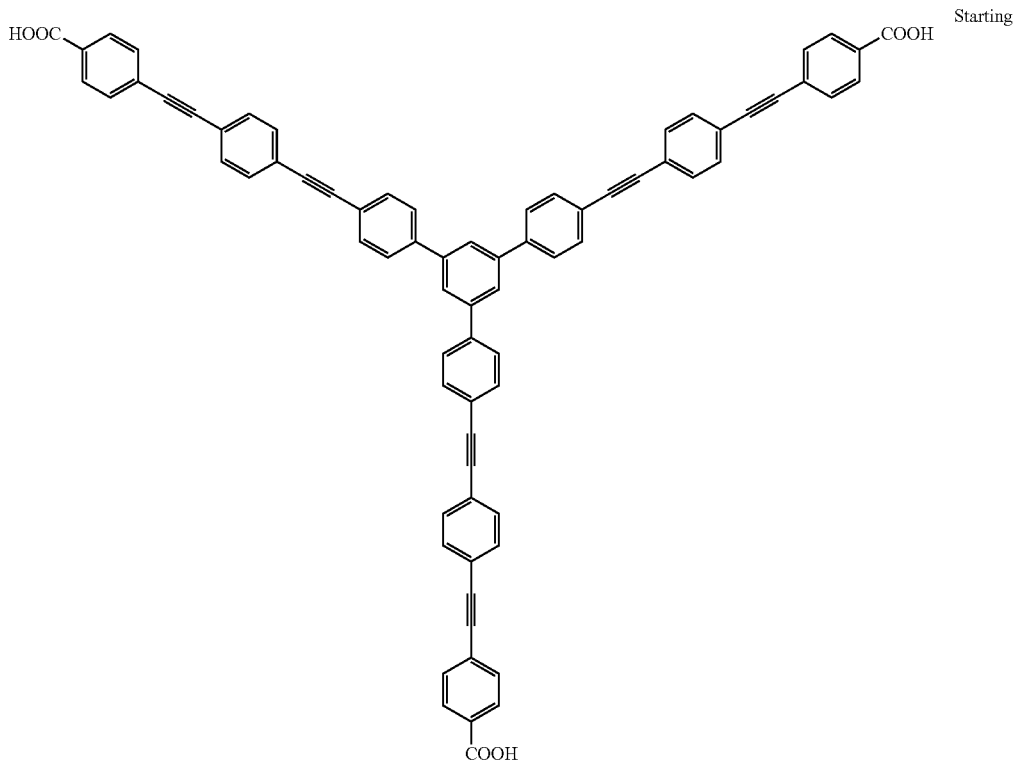

Starting material A2

-continued

[Chem. 11]

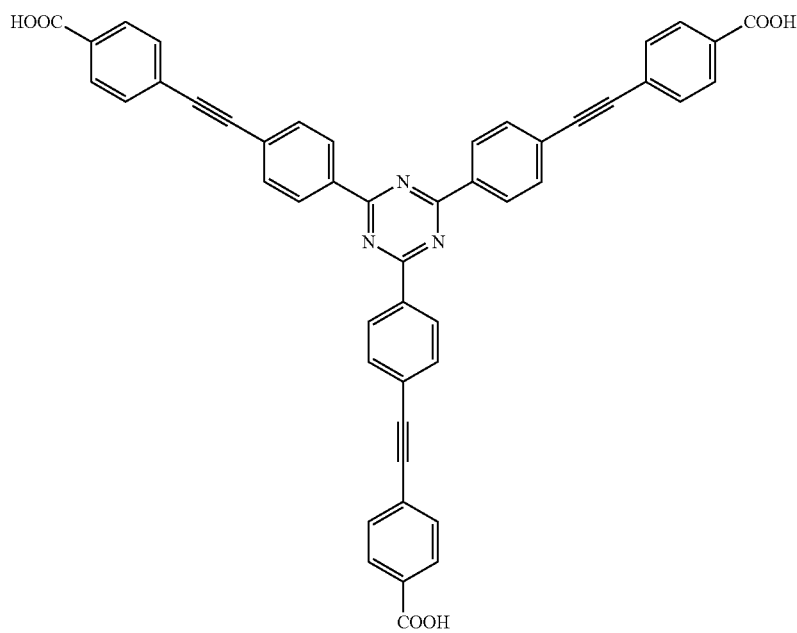

Starting material B

[Chem. 12]

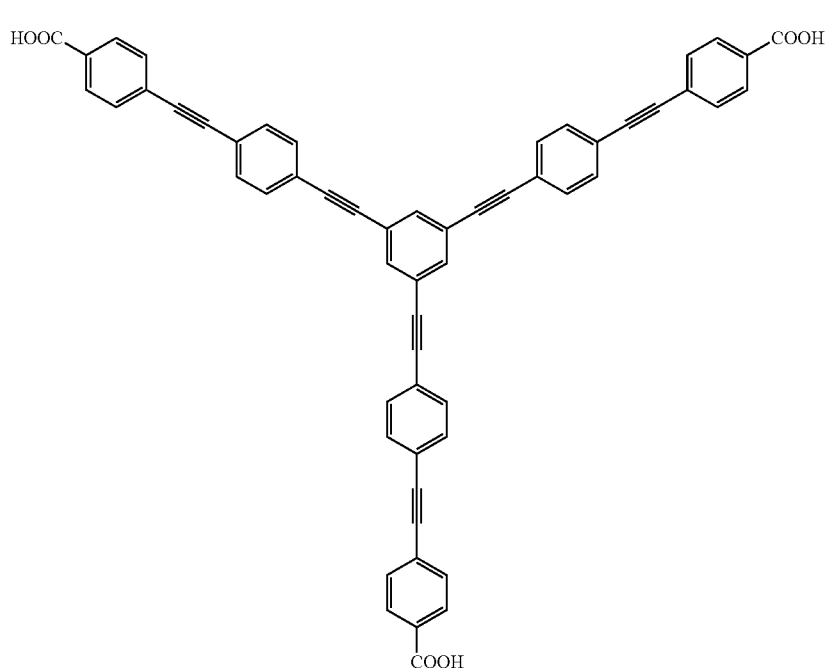

Starting material C

Hereinafter, a method and a device for storing a gas using the porous coordination polymer 1 according to the present embodiment will be described.

Figure 2:
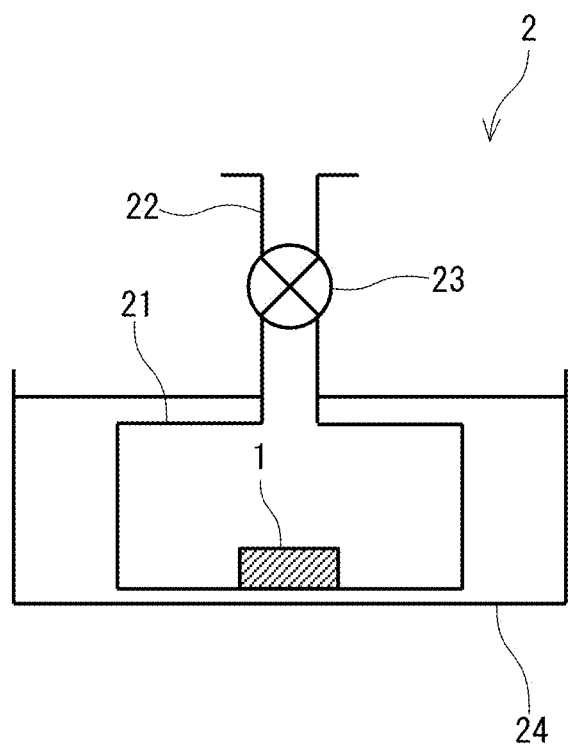
FIG. 2 shows a schematic view of a gas storage device comprising the porous coordination polymer according to the embodiment.

FIG. 2 shows a schematic view of a gas storage device 2 2 comprising the porous coordination polymer 1 according to the present embodiment. The gas storage device 2 comprises a sealed container 21 such as a gas bottle, as shown in FIG. 2. The sealed container 21 comprises an inlet 22. The inlet 22 is provided with a valve 23.

The porous coordination polymer 1 according to the present embodiment is disposed in the inside of the sealed container 21. Then, a gas is supplied to the inside of the sealed container 21 through the inlet 22. The valve 23 is open during the supply of the gas. In this way, the porous coordination polymer 1 according to the present embodiment is brought into contact with the gas. The hydrogen molecule is stored in the porous coordination polymer 1.

The pressure and temperature of the gas during the contact with the porous coordination polymer 1 is not limited, as far as the gas is stored in the porous coordination polymer 1. As one example, the gas may have a pressure of more than 0 Pa and not more than $10 \times 10^6$ Pa. The gas may have a temperature of not less than 0 degrees Celsius and not more than 50 degrees Celsius (desirably, room temperature of approximately 25 degrees Celsius).

The gas storage device 2 may comprise a thermostat 24. The thermostat 24 is located around the sealed container 21 and maintains the temperature of the sealed container 21 at a constant temperature. An example of the thermostat 24 is a thermostat bath in which water is stored. At least a part of the sealed container 21 is immersed in the water stored in the thermostat bath. The temperature of the water is maintained at a constant temperature.

When the inside of the sealed container 21 is heated, the gas which has been stored in the porous coordination polymer 1 according to the present embodiment is released. Also when the inside of the sealed container 21 is depressurized, the gas which has been stored in the porous coordination polymer 1 according to the present embodiment is released. The heating and the depressurizing may be conducted at the same time. Specifically, the porous coordination polymer 1 in which the gas has been stored may be left under a predetermined pressure (e.g., not less than 0 Pa and not more than $10 \times 10^6$ Pa) to release the gas. The temperature of the inside of the sealed container 21 during the release of the gas is not less than 0 degrees Celsius and not more than 50 degrees Celsius. In this way, the gas is released out of the sealed container 21 through the inlet 22. The valve 23 is open during the release of the gas.

The gas which can be stored in the porous coordination polymer 1 according to the present embodiment is at least one gas selected from the group consisting of a hydrogen gas and a hydrocarbon gas. The hydrogen gas contains many hydrogen molecules. Similarly, the hydrocarbon gas contains many hydrocarbon molecules each represented by the chemical formula $C_nH_m$ (where n is an integer of not less than 1 and not more than 4). When the value of n is equal to 1, the value of m is equal to 4. When the value of n is equal to 2, 3, or 4, the value of m is equal to (2n−2), (2n), or (2n+2)). In particular, it is desirable that the porous coordination polymer 1 according to the embodiment is used for storing the hydrogen gas. In other words, the porous coordination polymer 1 according to the embodiment can be used as a gas storage medium.

EXAMPLES

Hereinafter, the porous coordination polymer according to the present disclosure will be described in more detail with reference to the following examples.

Inventive Example 1

(Synthesis of the Porous Coordination Polymer PMOF-1)

In the inventive example 1, the porous coordination polymer PMOF-1 represented by the chemical formula (I) in which the value of X is equal to 1 was synthesized as below.

The following three reagents were added to a glass tube having a capacity of 30 mL to provide a mixture.

| | |
|---|---|
| N,N-dimethylformamide | 20 milliliters (purchased from Wako Pure Chemical Industries, Ltd., infinity pure grade) |
| Zinc nitrate terahydrates | 0.5 grams (purchased from Merck KGaA) |
| Tricarboxylic acid starting material A1 | 0.5 grams (purchased from Nard Institute, ltd.) |

[Chem. 13]

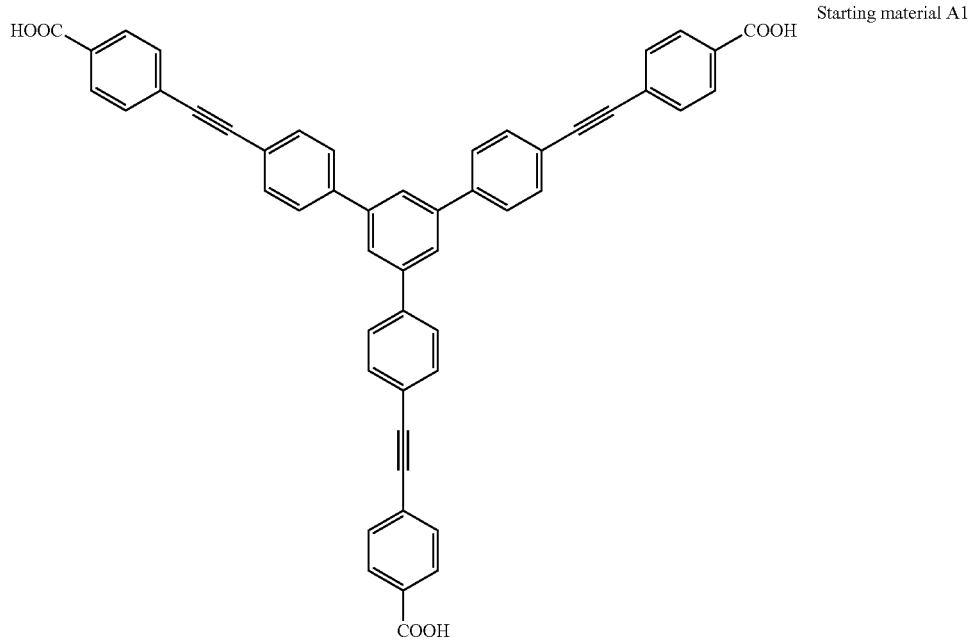

Starting material A1

Figure 3:
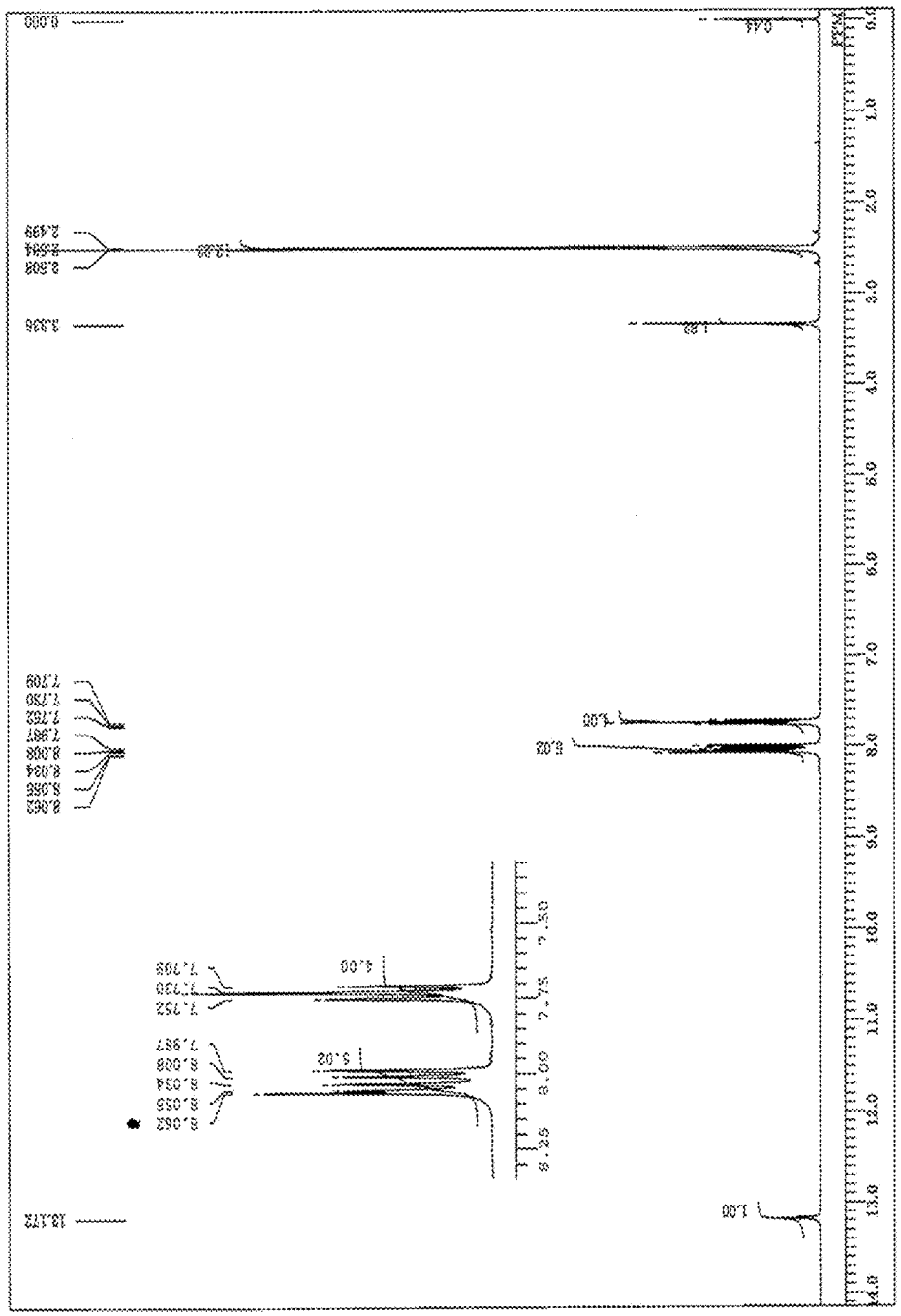
FIG. 3 shows an NMR spectrum of a tricarboxylic acid starting material A1 used in the inventive example 1.

FIG. 3 shows an NMR spectrum of the tricarboxylic acid starting material A1.

Then, the mixture was stirred to provide a solution. After covering the glass tube with the lid, the solution was left at rest at 100 degrees Celsius for 72 hours. During this period of 72 hours, $Zn_4O^{6+}$ clusters were formed first, and then, a carboxyl group ion contained in the ligand A1 (i.e., a tricarboxylic acid ion) shown below was bound to the $Zn_4O^{6+}$ cluster. This coordinate bond was repeated, and a polymer which was finally formed three-dimensionally was precipitated as the porous coordination polymer PMOF-1.

10 Pa for twenty-four hours. In this way, the porous coordination polymer PMOF-1 was provided.

[Chem. 14]

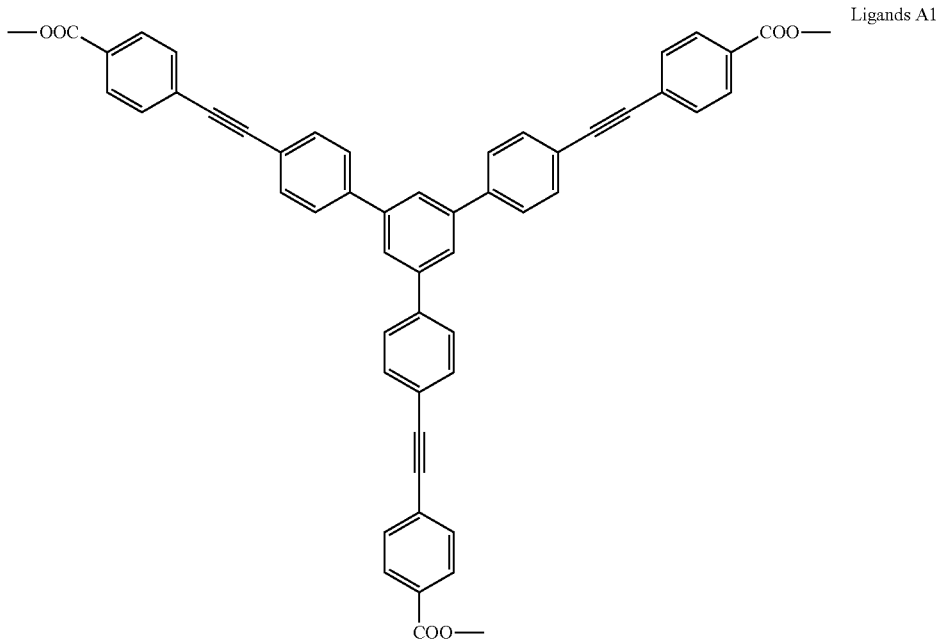

Ligands A1

(Washing, Namely, Purification, of the Porous Coordination Polymer PMOF-1)

Next, the porous coordination polymer PMOF-1 was washed as below. First, the solution in which the porous coordination polymer PMOF-1 was precipitated was moved to a centrifuge tube having a capacity of 50 mL. The solution was centrifuged at gravity acceleration of approximately 7,200 G. The supernatant was removed and the precipitate was left in the centrifuge tube. Then, N,N-dimethylformamide (20 milliliters) was added to the centrifuge tube to provide a solution. Then, the solution was stirred for one hour. The solution was centrifuged at gravity acceleration of approximately 7,200 G. Then, N,N-dimethylformamide (i.e., supernatant) was removed. This was repeated once again.

Then, methanol (20 milliliters) was added to the centrifuge tube to provide a solution. Then, the solution was stirred for one hour. The solution was centrifuged at gravity acceleration of approximately 7,200 G. Then, methanol (i.e., supernatant) was removed. This was repeated once again.

Furthermore, dichloromethane (20 milliliters) was added to the centrifuge tube to provide a solution. Then, the solution was stirred for one hour. The solution was centrifuged at gravity acceleration of approximately 7,200 G. Then, dichloromethane was removed. Subsequently, dichloromethane (20 milliliters) was added to the centrifuge tube to provide a solution. Then, the solution was stirred for 12 hours. The solution was centrifuged at gravity acceleration of approximately 7,200 G. Then, dichloromethane was removed.

In this way, the porous coordination polymer PMOF-1 was washed. In other words, the porous coordination polymer PMOF-1 was purified. The purified porous coordination polymer PMOF-1 was dried in a vacuum of not more than (Identification of the Structure of the Porous Coordination Polymer PMOF-1)

Figure 4:
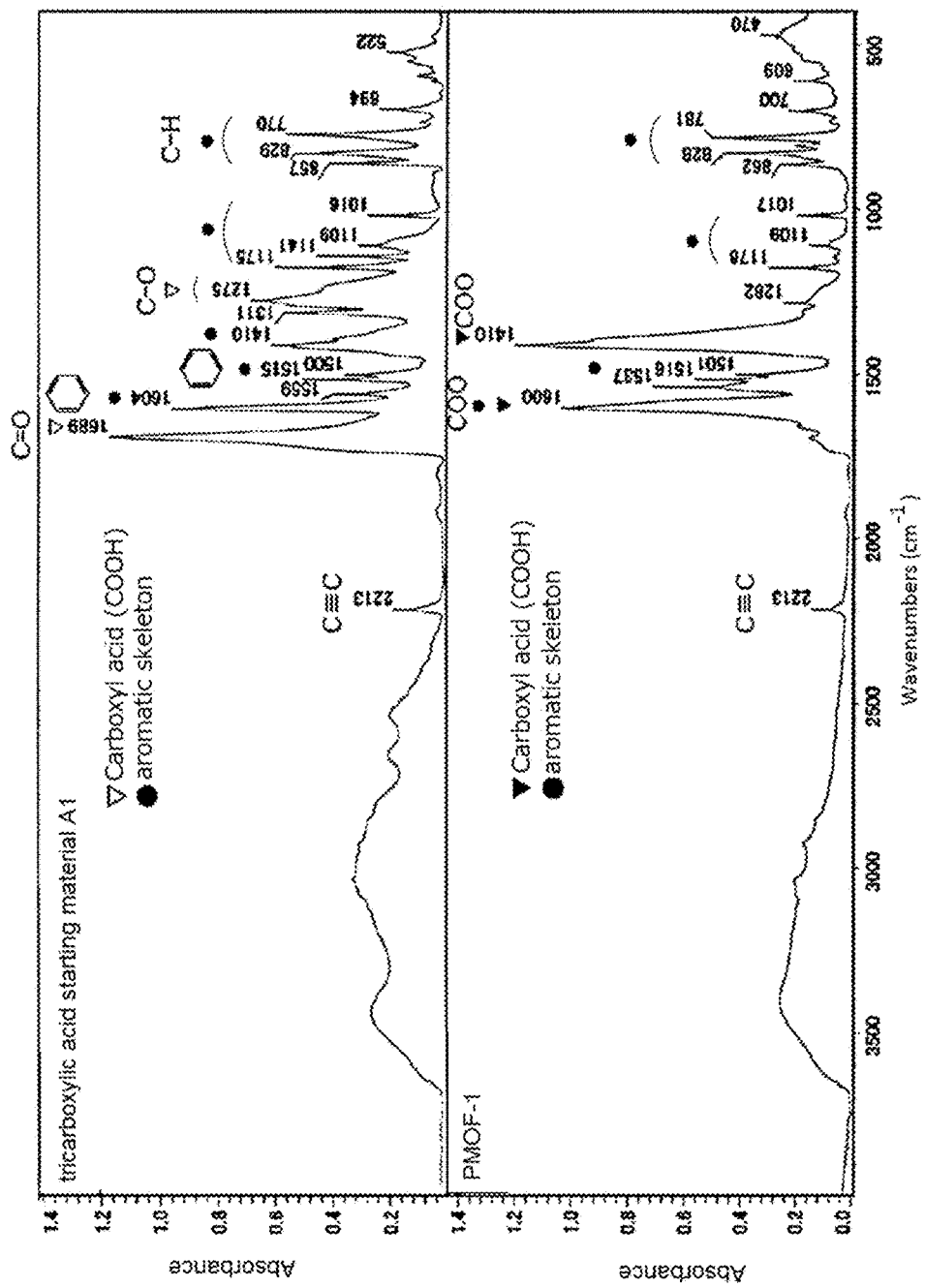
FIG. 4 shows an IR spectrum of the porous coordination polymer PMOF-1 synthesized in the inventive example 1 and an IR spectrum of the tricarboxylic acid starting material A1 used in the inventive example 1.

The above-provided porous coordination polymer PMOF-1 was subjected to an X-ray diffraction analysis. FIG. 5B shows an XRD spectrum of the porous coordination polymer PMOF-1. Furthermore, the porous coordination polymer PMOF-1 was also subjected to an infrared spectroscopic analysis. FIG. 4 shows an IR spectrum of the porous coordination polymer PMOF-1 and an IR spectrum of the tricarboxylic acid starting material A1.

As will be described below, the present inventors compared the peaks included in the XRD spectrum of the porous coordination polymer PMOF-1 synthesized actually in the inventive example 1 (hereinafter, such peaks are referred to as "actual peaks") with the peaks of the XRD spectrum of the porous coordination polymer PMOF-1 predicted on the basis of the structure of the porous coordination polymer MOF-177 (hereinafter, such peaks are referred to as "predicted peaks").

On the basis of the peaks included in the XRD spectrum of the porous coordination polymer MOF-177 (see FIG. 5A), the present inventors calculated the 2θ values of the predicted peaks included in the XRD spectrum of the porous coordination polymer PMOF-1 as below.

Figure 6A:
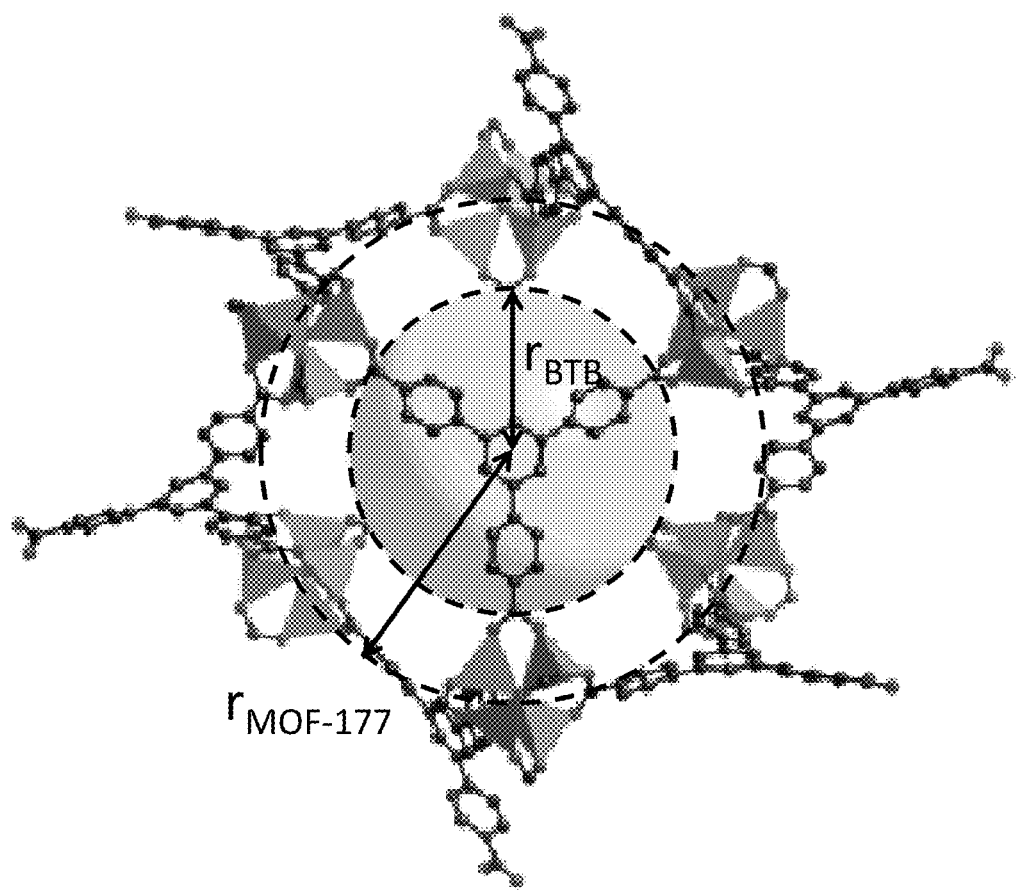
FIG. 6A shows a schematic view of the structure of the porous coordination polymer MOF-177.
Figure 6B:
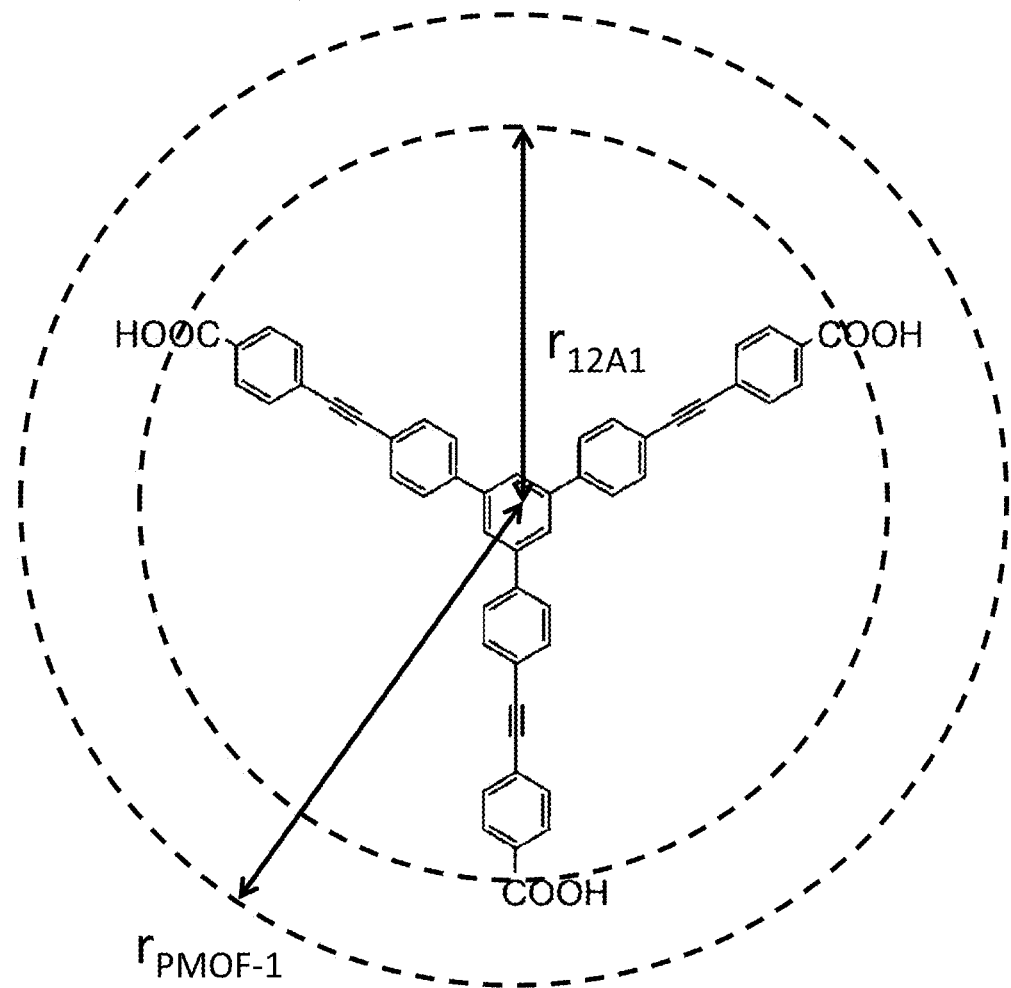
FIG. 6B shows a schematic view of the structure of the porous coordination polymer PMOF-1 under presumption that the porous coordination polymer PMOF-1 has the same structure as the porous coordination polymer MOF-177.

FIG. 6A shows a schematic view of the structure of the porous coordination polymer MOF-177. FIG. 6B shows a schematic view of the structure of the porous coordination polymer PMOF-1 under presumption that the porous coordination polymer PMOF-1 has the same structure as the porous coordination polymer MOF-177.

The present inventors calculated the radius $r_{BTB}$ of the ligand of the porous coordination polymer MOF-177 shown in FIG. 6A, on the basis of the atomic bond distance shown in the following Table 1. Hereinafter, the ligand of the porous coordination polymer MOF-177 is referred to as "ligand BTB". As a result, the radius $r_{BTB}$ of the ligand BTB was 0.863 nanometers. The radius $r_{BTB}$ was calculated under presumption that the center of the benzene ring (i.e., an aryl group) located at the center of the ligand BTB accords with the center of the ligand BTB.

TABLE 1

|  | Distance |
| --- | --- |
| C—C | 0.163 nanometers |
| C=C (aromatic series) | 0.140 nanometers |
| C≡C | 0.119 nanometers |
| C=O (carboxylic acid) | 0.140 nanometers |
| Zn$_4$O (radius) | 0.197 nanometers |

Likewise, the present inventors also calculated the radius $r_{12A1}$ of the terdentate ligand 12 included in the porous coordination polymer PMOF-1. The radius $r_{12A1}$ was 1.568 nanometers.

Then, on the basis of the values of the radius $r_{BTB}$ and the radius of Zn$_4$O shown in Table 1, the present inventors calculated the radius $r_{MOF-177}$ of the porous coordination polymer MOF-177 (namely, the distance between the center and the periphery of the porous coordination polymer MOF-177 including the Zn$_4$O$^{6+}$ clusters). The radius $r_{MOF-177}$ was 1.06 nanometers.

Likewise, the present inventors also calculated the radius $r_{PMOF-1}$ of the porous coordination polymer PMOF-1 (namely, the distance between the center and the periphery of the porous coordination polymer PMOF-1 including the Zn$_4$O$^{6+}$ clusters). The radius $r_{PMOF-1}$ was 1.765 nanometers. The radius $r_{PMOF-1}$ indicated in FIG. 6B is equal to a half of the case size (See FIG. 1) in the inventive example 1.

Under presumption that the porous coordination polymer PMOF-1 has the same structure as the porous coordination polymer MOF-177 and that both of the porous coordination polymers have the same XRD spectrum shape as each other, the present inventors calculated the 2θ values at which the predicted peaks appear in the XRD spectrum of the porous coordination polymer PMOF-1 on the basis of the following three values.

(Value (i)): Radius $r_{MOF-177}$ (namely, 1.06 nanometers)
(Value (ii)): Radius $r_{PMOF-1}$ (namely, 1.765 nanometers)
(Value (iii)): 2θ values at which the peaks appear in the XRD spectrum of the porous coordination polymer MOF-177 (see FIG. 5A).

Since the mathematical formula "$n\lambda=2d\cdot\sin\theta$" is satisfied on the basis of the Bragg's law, the following mathematical formula (IV1) is satisfied.

$$2k(1.06 \text{ nanometers})\cdot\sin\theta_1 = 2k(1.765 \text{ nanometers})\cdot\sin\theta_2 \quad \text{(IV1)}$$

where
$\theta_1$ represents a diffraction angle of the porous coordination polymer MOF-177,
$\theta_2$ represents a diffraction angle of the porous coordination polymer PMOF-1, and
k represents an integer.

The following mathematical formula (V1) is satisfied on the basis of the mathematical formula (IV1).

$$\sin\theta_2 = 1.06(\sin\theta_1)/1.765 \quad \text{(V1)}$$

Figure 5A:
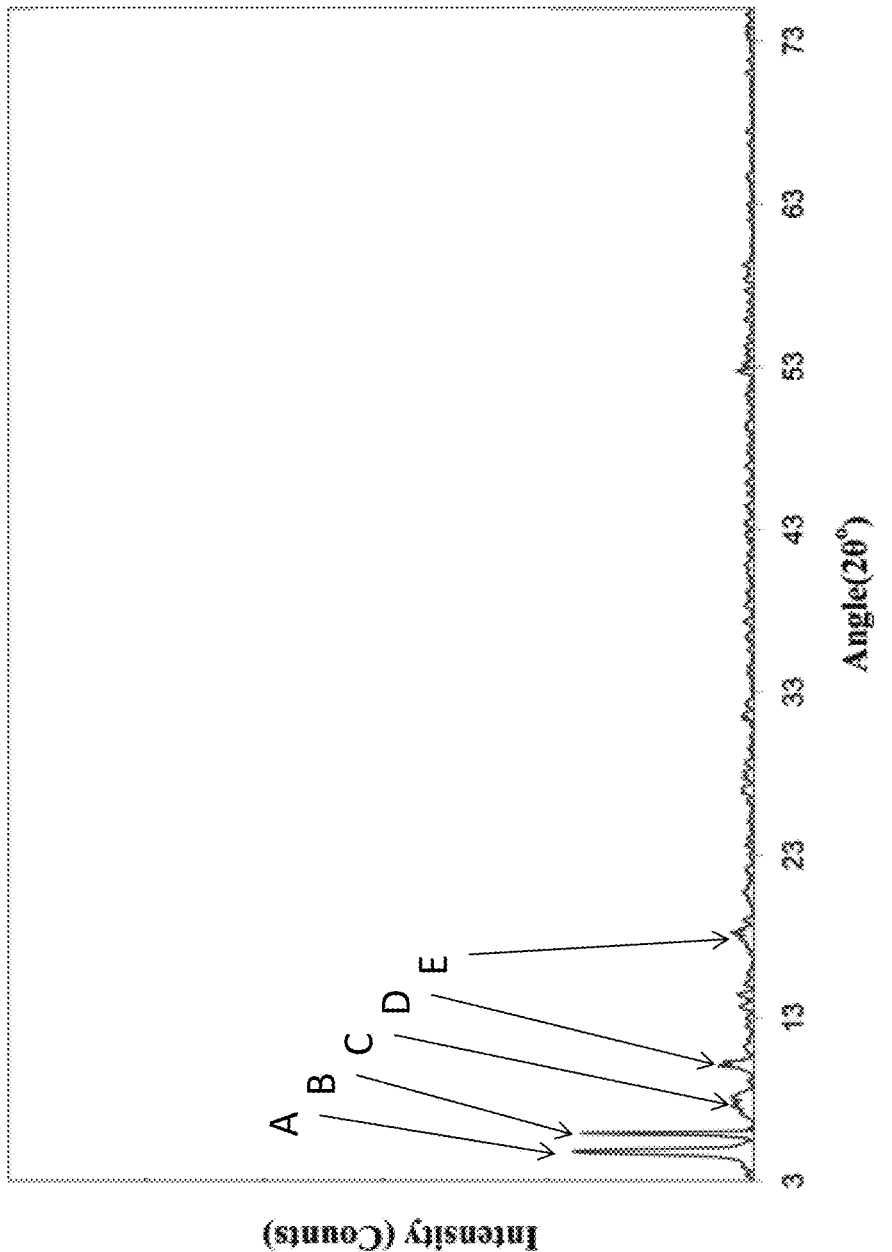
FIG. 5A shows an XRD spectrum of the porous coordination polymer MOF-177 disclosed in Dipendu Saha et. al., "Structural Stability of Metal Organic Framework MOF-177", Journal of Physics Chemical Letters, 2010, 1(1), pp. 73-78.
Figure 5B:
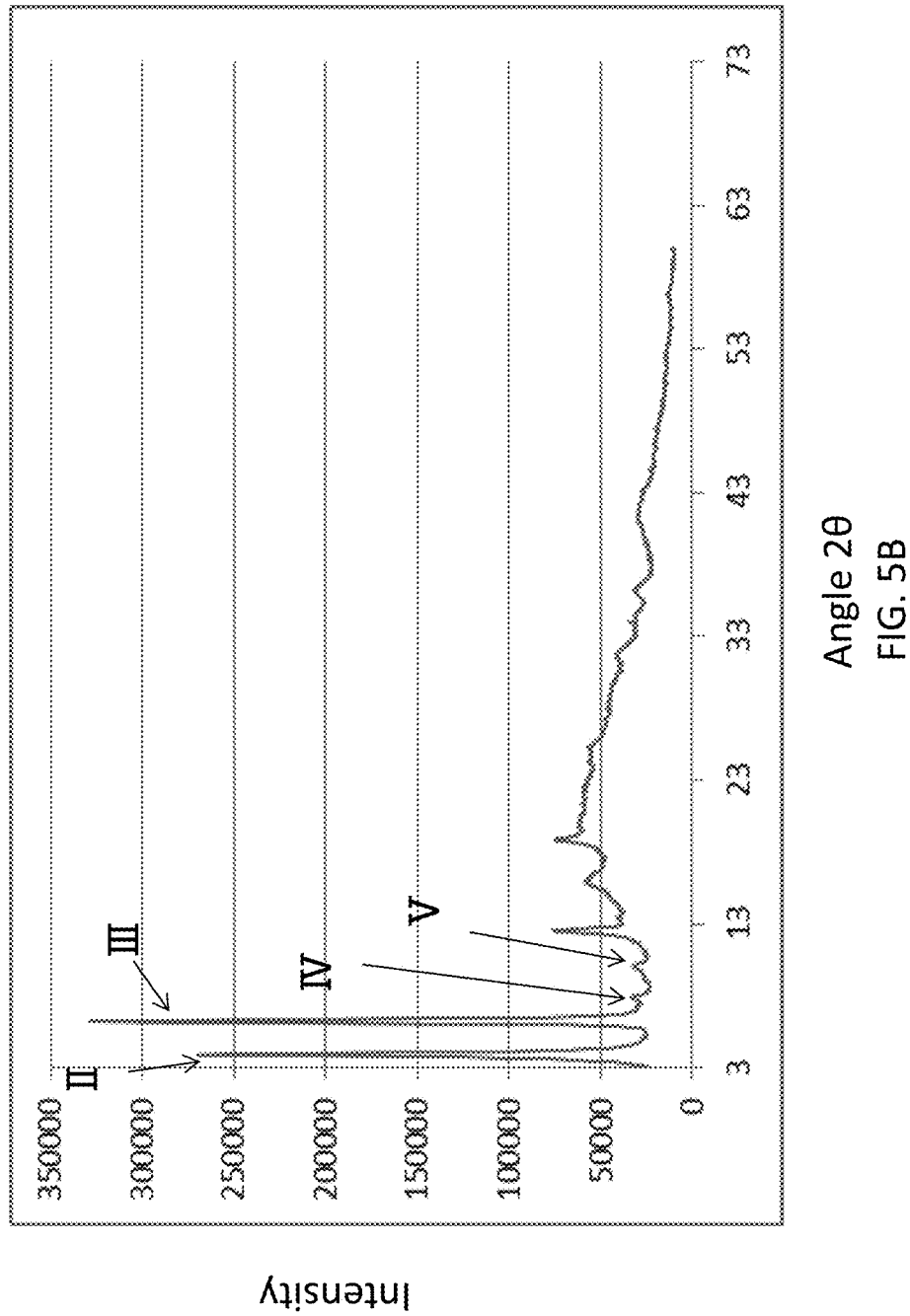
FIG. 5B shows an XRD spectrum of the porous coordination polymer PMOF-1 synthesized actually in the inventive example 1.

FIG. 5A shows an XRD spectrum of the porous coordination polymer MOF-177 disclosed in Dipendu Saha et. al., "Structural Stability of Metal Organic Framework MOF-177", Journal of Physics Chemical Letters, 2010, 1 (1), pp. 73-78. Since the value of 2θ$_1$ is equal to 5.2° at the peak A included in FIG. 5A, the following mathematical formula (VI1) is satisfied on the basis of the mathematical formula (V1).

$$\sin\theta_2 = 1.06(\sin(5.2/2))/1.765 \quad \text{(VI1)}$$

Therefore, the value 2θ$_2$ is equal to 3.1°.

Likewise, at the peaks B, C, D, and E included in FIG. 5A, the values 2θ$_1$ are equal to 6.9°, 10.9°, 13.2°, and 18.0°, respectively. Therefore, on the basis of the mathematical formula (V1), the four mathematical formulas 2θ$_2$=4.1°, 2θ$_2$=6.5°, 2θ$_2$=7.9°, and 2θ$_2$=10.8°.

FIG. 5B shows an XRD spectrum of the porous coordination polymer PMOF-1 synthesized actually in the inventive example 1. The above-predicted five 2θ$_2$ values accord substantially with the values 2θ of the peaks II, III, IV, and V included in the XRD spectrum of the porous coordination polymer PMOF-1 synthesized actually in the inventive example 1. In FIG. 5B, the peak I which corresponds to the 2θ$_2$ value of 3.1° does not appear. This is due to measurement limit of the XRD spectrum measurement device. This does not mean that the peak I which corresponds to the peak A did not appear.

As is clear from the comparison of FIG. 5B with FIG. 5A, the 2θ$_2$ values of the peaks II, III, IV, and V of the porous coordination polymer PMOF-1 are smaller than the 2θ$_1$ values of the peaks B, C, D, and E of the porous coordination polymer MOF-177, respectively. This means that the pore size and the cage size of the porous coordination polymer PMOF-1 is larger than those of the porous coordination polymer MOF-177.

As shown in FIG. 4, in the IR spectrum of the porous coordination polymer PMOF-1, the peaks of the carboxyl acid included in the starting material A1 was changed to the peaks of the carboxylate.

On the basis of the above results, the present inventors believe that the porous coordination polymer PMOF-1 has the same structure as the porous coordination polymer MOF-177.

(Ability of Storing Hydrogen Molecules of the Porous Coordination Polymer PMOF-1)

The porous coordination polymer PMOF-1 (100 mg) provided in the inventive example 1 was put in a glass cell. Then, the inside of the glass cell was depressurized to vacuum at a temperature of 60 degrees Celsius. In this way, the gas contained in the porous coordination polymer PMOF-1 was removed.

The glass cell was immersed in a thermostat bath. The temperature in the thermostat bath was maintained at room temperature (i.e., approximately 25 degrees Celsius). While the glass cell was immersed in the thermostat bath, the pressure of hydrogen contained in the glass cell was gradually increased using a gas adsorption measurement device (purchased from Suzuki Shokan Co., Ltd, trade name: PCT measurement system). After the pressure of the hydrogen which had been supplied to the glass cell reached 10×10$^6$ Pa, the pressure of the hydrogen contained in the glass cell was gradually decreased.

Figure 7:
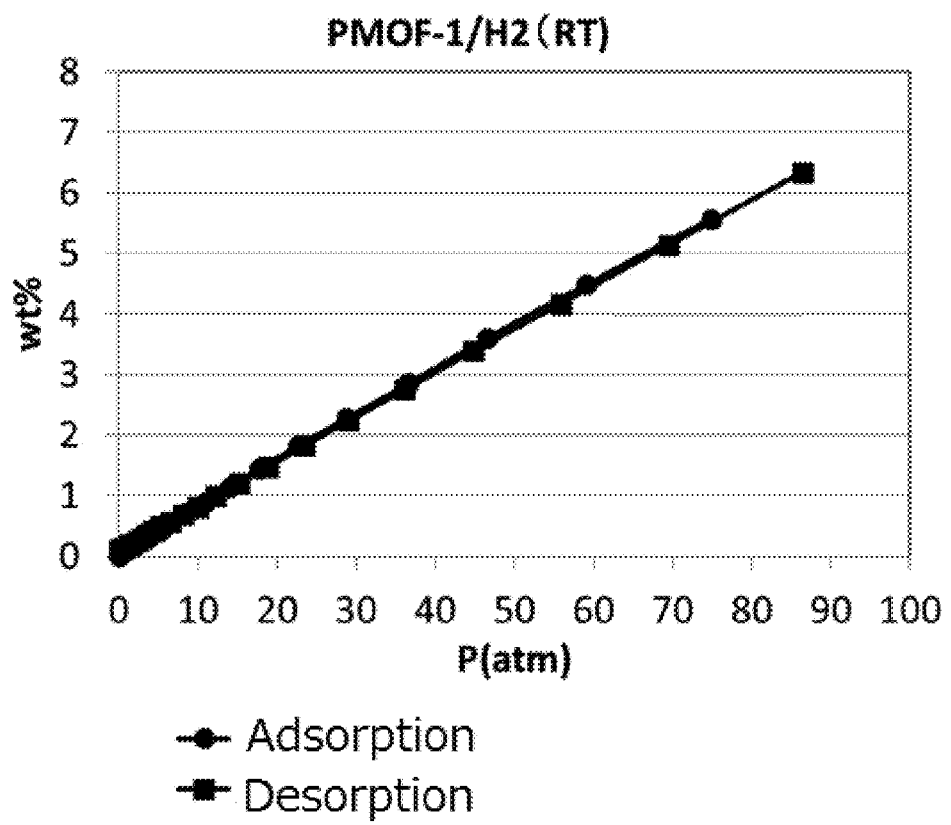
FIG. 7 is a graph showing the results of the hydrogen adsorption-desorption experience of the porous coordination polymer PMOF-1 synthesized in the inventive example 1.

FIG. 7 shows a graph showing the results of this experiment. As is clear from FIG. 7, the porous coordination polymer PMOF-1 has high ability of hydrogen adsorption-desorption.

Inventive Example 2

(Synthesis of the Porous Coordination Polymer PMOF-5)

In the inventive example 2, the porous coordination polymer PMOF-5 represented by the chemical formula (I) in which the value of X is equal to 2 was synthesized as below.

The following three reagents were added to a glass tube having a capacity of 30 mL to provide a mixture.

| | |
|---|---|
| N,N-dimethylformamide | 20 milliliters (purchased from Wako Pure Chemical Industries, Ltd., infinity pure grade) |
| Zinc nitrate terahydrates | 0.5 grams (purchased from Merck KGaA) |
| Tricarboxylic acid starting material A2 | 0.5 grams (purchased from Nard Institute, ltd.) |

[Chem. 15]

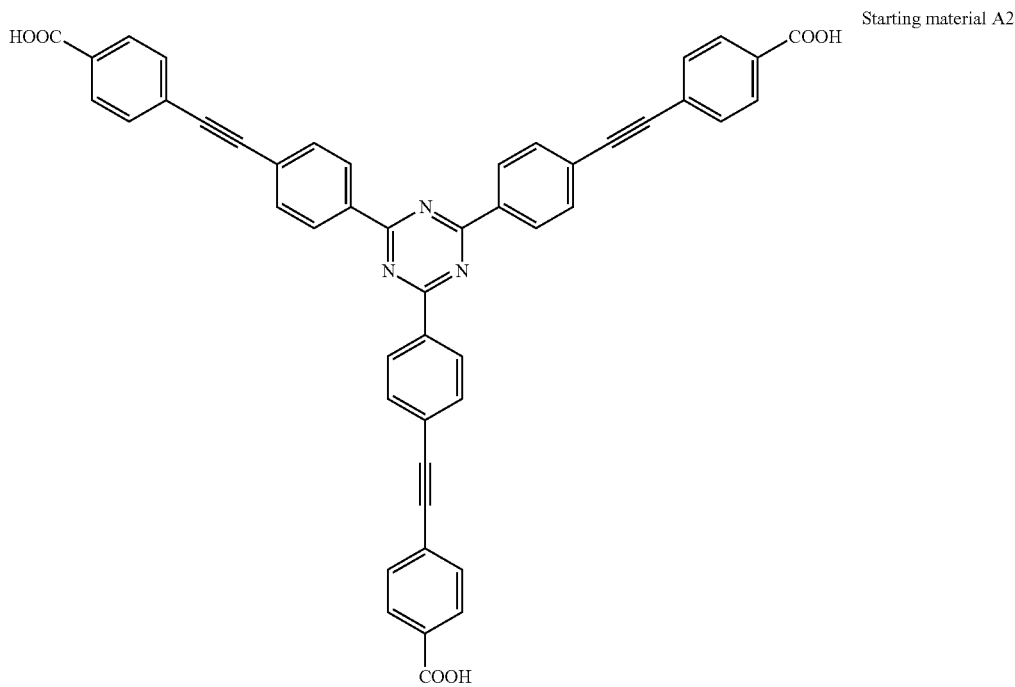

Starting material A2

Figure 8:
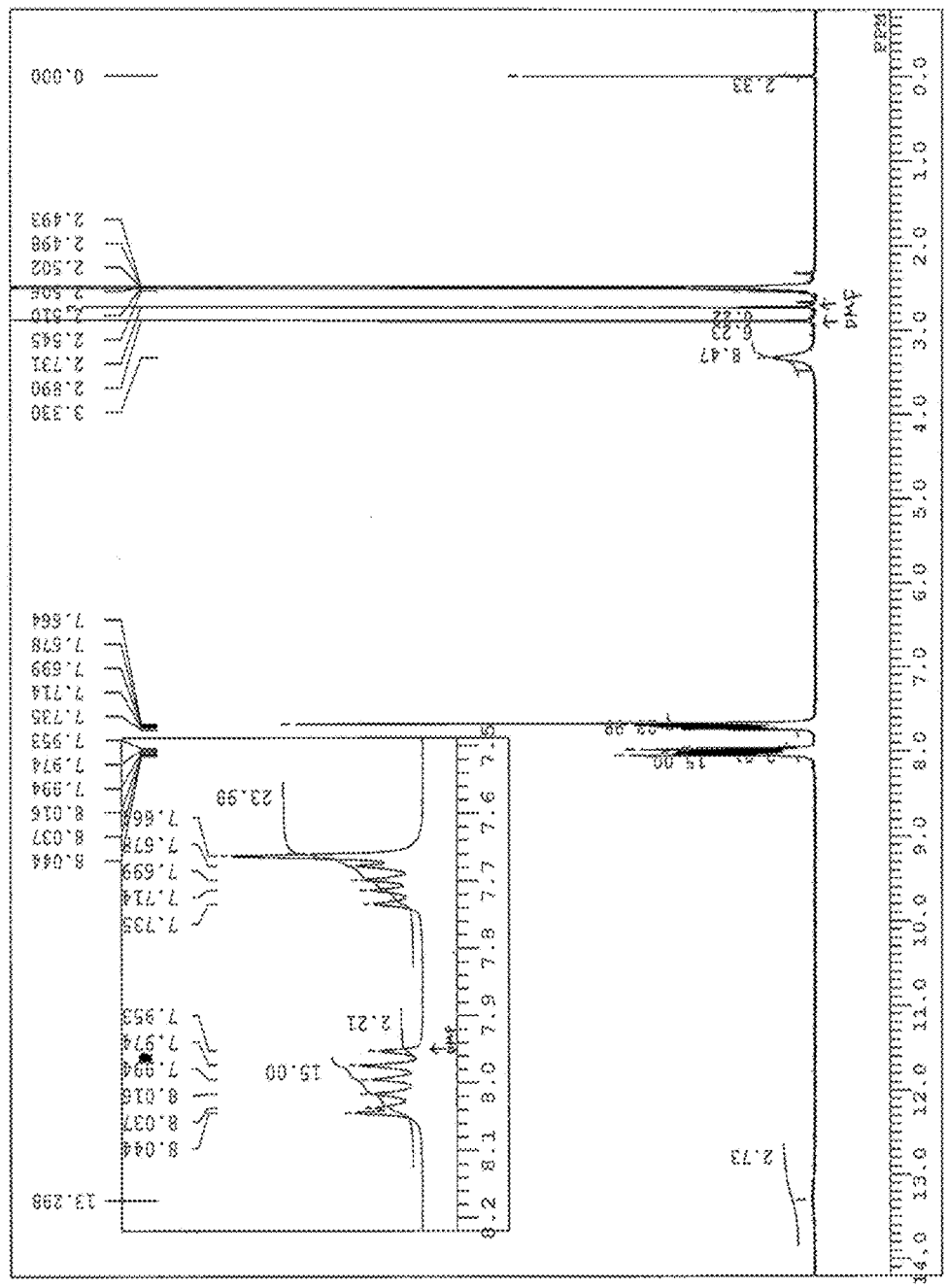
FIG. 8 shows an NMR spectrum of a tricarboxylic acid starting material A2 used in the inventive example 2.

FIG. 8 shows an NMR spectrum of the tricarboxylic acid starting material A2.

Then, the mixture was stirred to provide a solution. After covering the glass tube with the lid, the solution was left at rest at 100 degrees Celsius for 72 hours. During this period of 72 hours, $Zn_4O^{6+}$ clusters were formed first, and then, a carboxyl group ion contained in the ligand A2 (i.e., a tricarboxylic acid ion) shown below was bound to the $Zn_4O^{6+}$ cluster. This coordinate bond was repeated, and a polymer which was finally formed three-dimensionally was precipitated as the porous coordination polymer PMOF-5.

[Chem. 16]

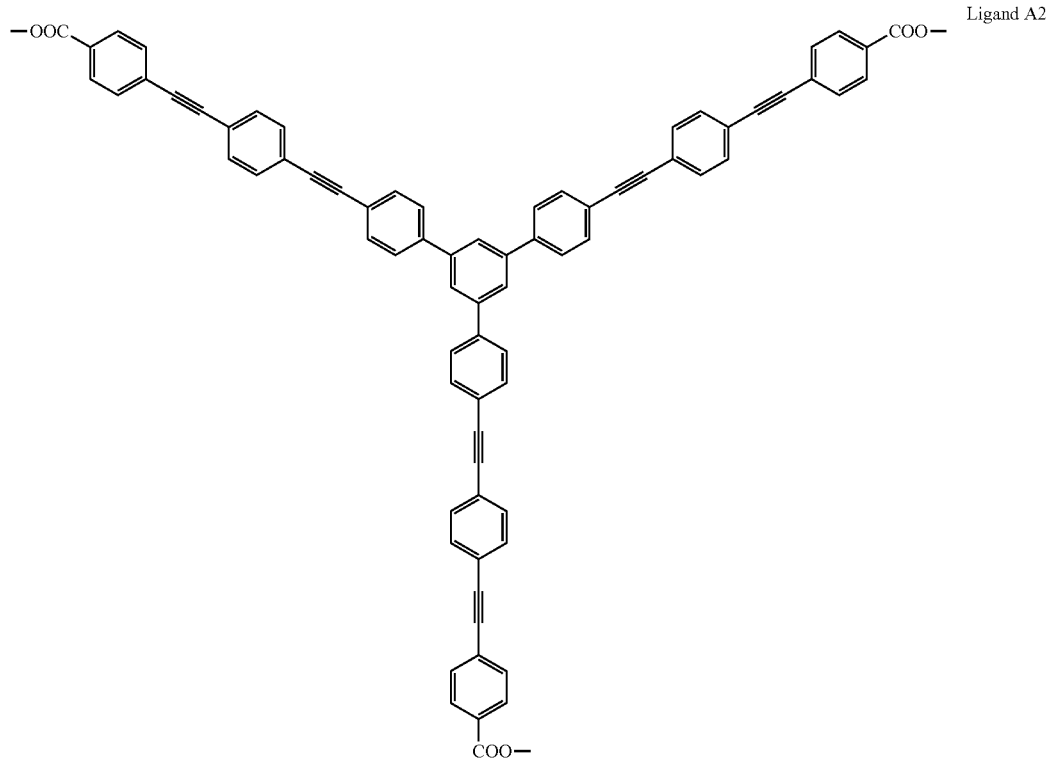

Ligand A2

Then, the porous coordination polymer PMOF-5 was purified similarly to the case of the inventive example 1.

(Identification of the Structure of the Porous Coordination Polymer PMOF-5)

Figure 9:
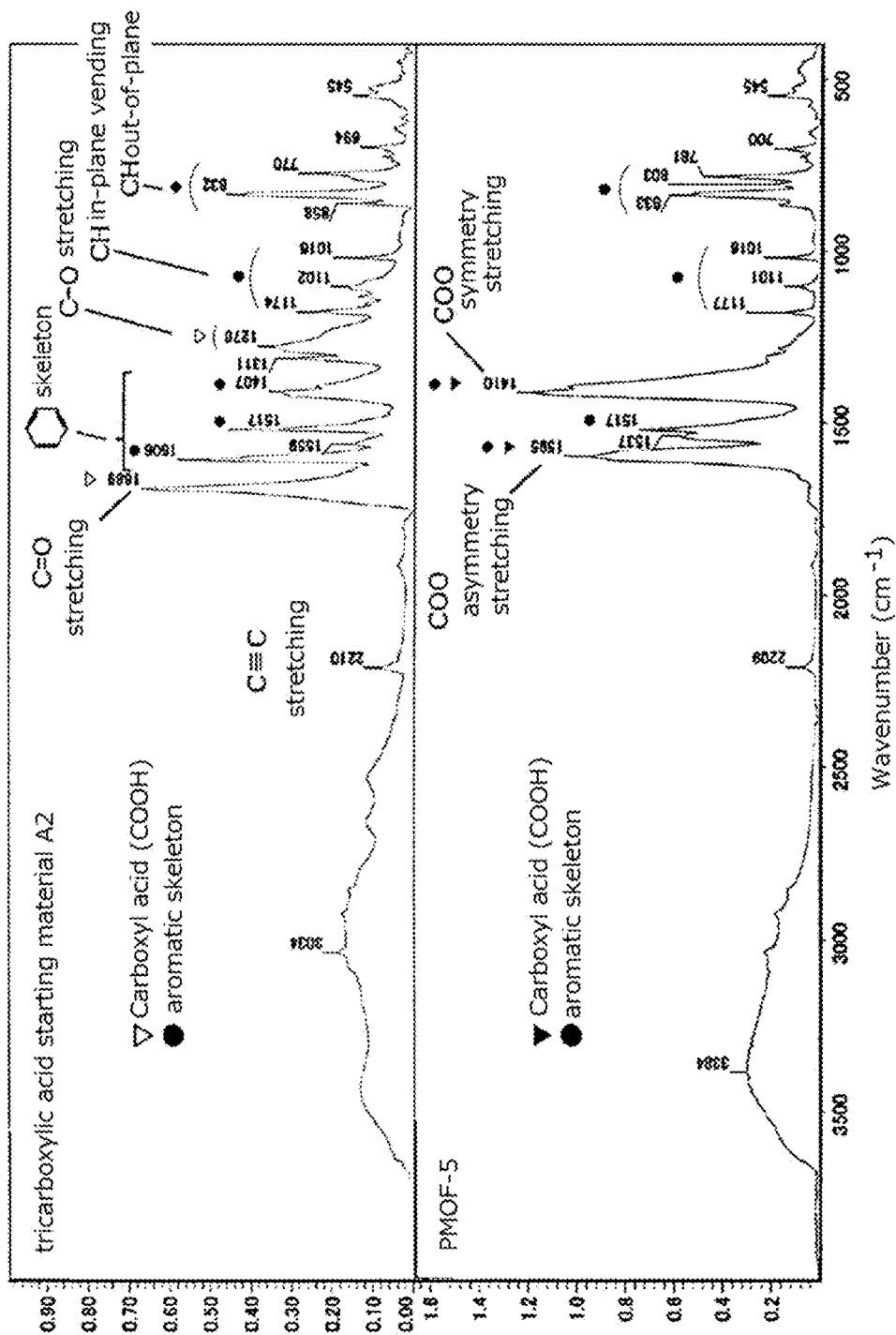
FIG. 9 shows an IR spectrum of the porous coordination polymer PMOF-5 synthesized in the inventive example 2 and an IR spectrum of the tricarboxylic acid starting material A2 used in the inventive example 2.
Figure 10:
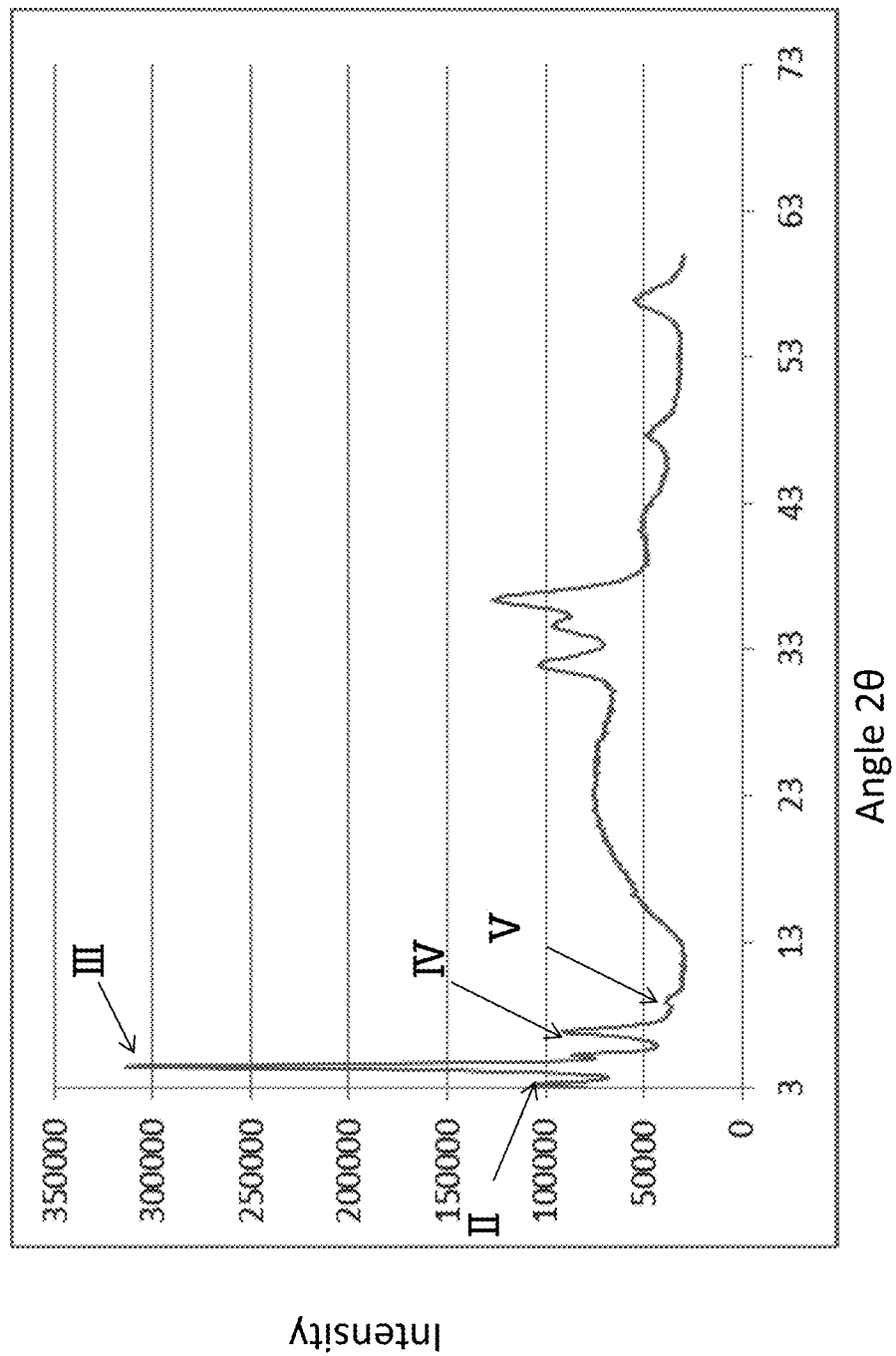
FIG. 10 shows an XRD spectrum of the porous coordination polymer PMOF-5 synthesized actually in the inventive example 2.

The above-provided porous coordination polymer PMOF-5 was subjected to an X-ray diffraction analysis. FIG. 10 shows an XRD spectrum of the porous coordination polymer PMOF-5. Furthermore, the porous coordination polymer PMOF-5 was also subjected to an infrared spectroscopic analysis. FIG. 9 shows an IR spectrum of the porous coordination polymer PMOF-5 and an IR spectrum of the tricarboxylic acid starting material A2.

Similarly to the case of the inventive example 1, the present inventors compared the actual peaks included in the XRD spectrum of the porous coordination polymer PMOF-5 with the predicted peaks of the XRD spectrum predicted on the basis of the structure of the porous coordination polymer MOF-177.

The radius $r_{12A2}$ of the terdentate ligand 12 included in the porous coordination polymer PMOF-5 was 2.273 nanometers on the basis of the calculation with reference to Table 1.

Figure 11:
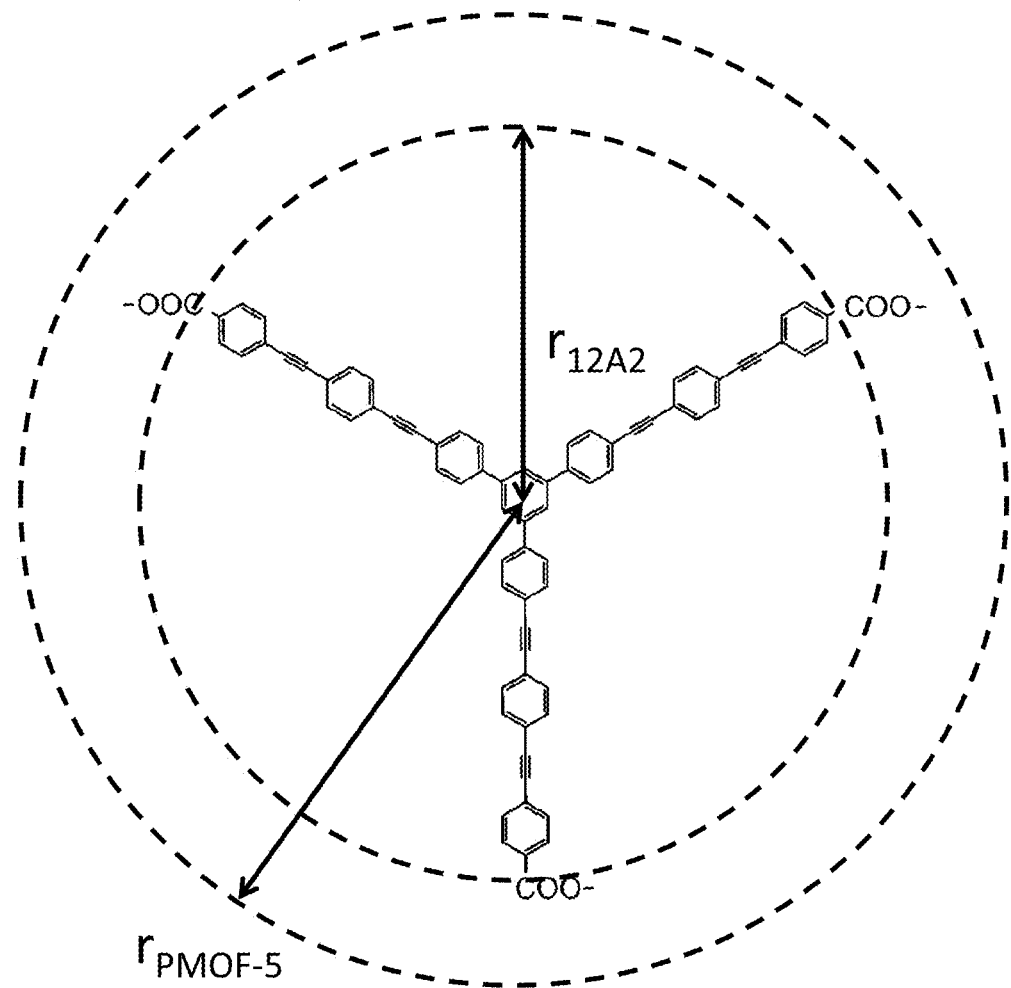
FIG. 11 shows a schematic view of the structure of the porous coordination polymer PMOF-5 under presumption that the porous coordination polymer PMOF-5 has the same structure as the porous coordination polymer MOF-177.

The radius $r_{MOF-5}$ of the porous coordination polymer PMOF-5 (namely, the distance between the center and the periphery of the porous coordination polymer PMOF-5 including the $Zn_4O^{6+}$ clusters) was 2.470 nanometers on the basis of the calculation with reference to Table 1. The radius $r_{PMOF-5}$ indicated in FIG. 11 is equal to a half of the case size (See FIG. 1) in the inventive example 2.

Under presumption that the porous coordination polymer PMOF-5 has the same structure as the porous coordination polymer MOF-177 and that both of the porous coordination polymers have the same XRD spectrum shape as each other, the present inventors calculated the 2θ values at which the predicted peaks appear in the XRD spectrum of the porous coordination polymer PMOF-5 on the basis of the following three values as below.

(Value (i)): Radius $r_{MOF-177}$ (namely, 1.06 nanometers)

(Value (ii)): Radius $r_{PMOF-5}$ (namely, 2.470 nanometers)

(Value (iii)): 2θ values at which the peaks appear in the XRD spectrum of the porous coordination polymer MOF-177 (see FIG. 5A).

FIG. 11 shows a schematic view of the structure of the porous coordination polymer PMOF-5 under presumption that the porous coordination polymer PMOF-5 has the same structure as the porous coordination polymer MOF-177.

Since the mathematical formula "$n\lambda=2d\cdot\sin\theta$" is satisfied on the basis of the Bragg's law, the following mathematical formula (IV2) is satisfied.

$$2k(1.06 \text{ nanometers})\cdot\sin\theta_1=2k(2.470 \text{ nanometers})\cdot\sin\theta_2 \quad (IV2)$$

where $\theta_1$ represents a diffraction angle of the porous coordination polymer MOF-177, $\theta_2$ represents a diffraction angle of the porous coordination polymer PMOF-5, and k represents an integer.

The following mathematical formula (V2) is satisfied on the basis of the mathematical formula (IV2).

$$\sin\theta_2=1.06(\sin\theta_1)/2.470 \quad (V2)$$

Since the value of $2\theta_1$ is equal to 5.2° at the peak A included in FIG. 5A, the following mathematical formula (VI2) is satisfied on the basis of the mathematical formula (V2).

$$\sin\theta_2 = 1.06(\sin(5.2/2))/2.470 \quad \text{(VI2)}$$

Therefore, the value $2\theta_2$ is equal to 2.2°.

Likewise, at the peaks B, C, D, and E included in FIG. 5A, the $2\theta_1$ values are equal to 6.9°, 10.9°, 13.2°, and 18.0°. Therefore, on the basis of the mathematical formula (V2), the four mathematical formulas $2\theta_2=3.0°$, $2\theta_2=4.6°$, $2\theta_2=5.7°$, and $2\theta_2=7.7°$ are satisfied.

FIG. 10 shows an XRD spectrum of the porous coordination polymer PMOF-5 synthesized actually in the inventive example 2. The above-predicted five $2\theta_2$ values accord substantially with the $2\theta_2$ values of the peaks II, III, IV, and V included in the XRD spectrum of the porous coordination polymer PMOF-5 synthesized actually in the inventive example 2. In FIG. 10B, the peak I which corresponds to the $2\theta_2$ value of 3.1° does not appear. This is due to measurement limit of the XRD spectrum measurement device. This does not mean that the peak I which corresponds to the peak A did not appear.

As is clear from the comparison of FIG. 10 with FIG. 5A, the $2\theta_2$ values of the peaks II, III, IV, and V of the porous coordination polymer PMOF-5 are smaller than the $2\theta_1$ values of the peaks B, C, D, and E of the porous coordination polymer MOF-177, respectively. This means that the pore size and the cage size of the porous coordination polymer PMOF-5 is larger than those of the porous coordination polymer MOF-177.

As shown in FIG. 9, in the IR spectrum of the porous coordination polymer PMOF-5, the peaks of the carboxyl acid included in the starting material A2 was changed to the peaks of the carboxylate.

On the basis of the above results, the present inventors believe that the porous coordination polymer PMOF-5 has the same structure as the porous coordination polymer MOF-177.

(Ability of Storing Hydrogen Molecules of the Porous Coordination Polymer PMOF-5)

Similarly to the case of the inventive example 1, the ability of storing hydrogen molecules of the porous coordination polymer PMOF-5 (100 mg) provided in the inventive example 2 was evaluated.

Figure 12:
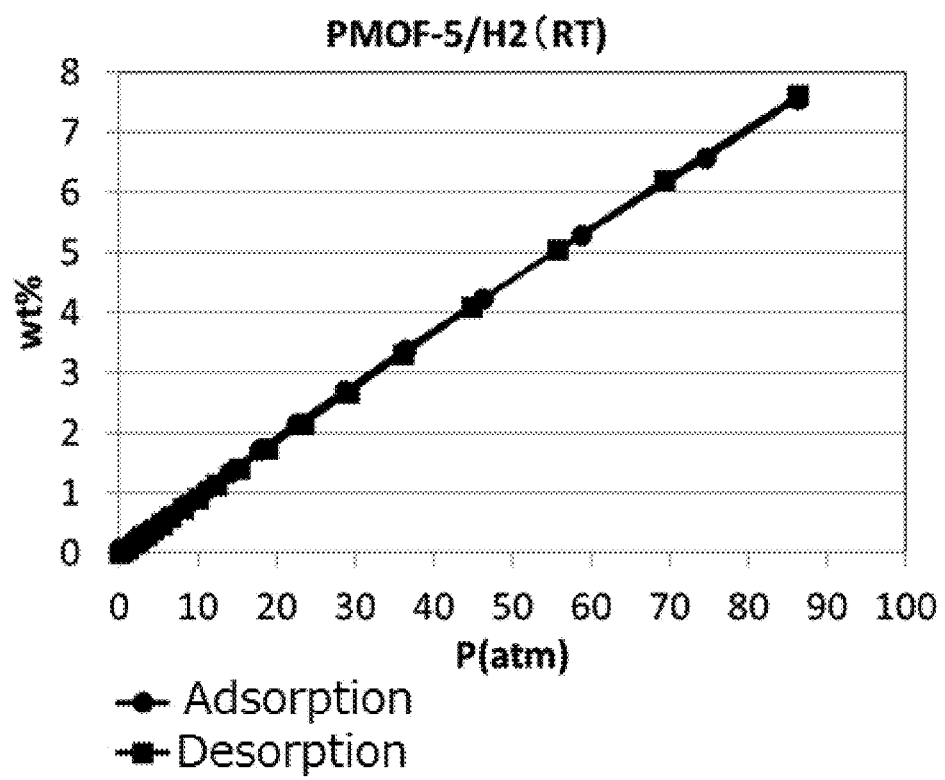
FIG. 12 is a graph showing the results of the hydrogen adsorption-desorption experience of the porous coordination polymer PMOF-5 synthesized in the inventive example 2.

FIG. 12 shows a graph showing the results of this experiment. As is clear from FIG. 12, the porous coordination polymer PMOF-5 has high ability of hydrogen adsorption-desorption.

Inventive Example 3

(Synthesis of the Porous Coordination Polymer PMOF-1N)

In the inventive example 3, the porous coordination polymer PMOF-1N represented by the chemical formula (II) in which the value of X is equal to 1 was synthesized as below.

The following three reagents were added to a glass tube having a capacity of 30 mL to provide a mixture.

| | |
|---|---|
| N,N-dimethylformamide | 20 milliliters (purchased from Wako Pure Chemical Industries, Ltd., infinity pure grade) |
| Zinc nitrate terahydrates | 0.5 grams (purchased from Merck KGaA) |
| Tricarboxylic acid starting material B | 0.5 grams (purchased from Nard Institute, ltd.) |

[Chem. 17]

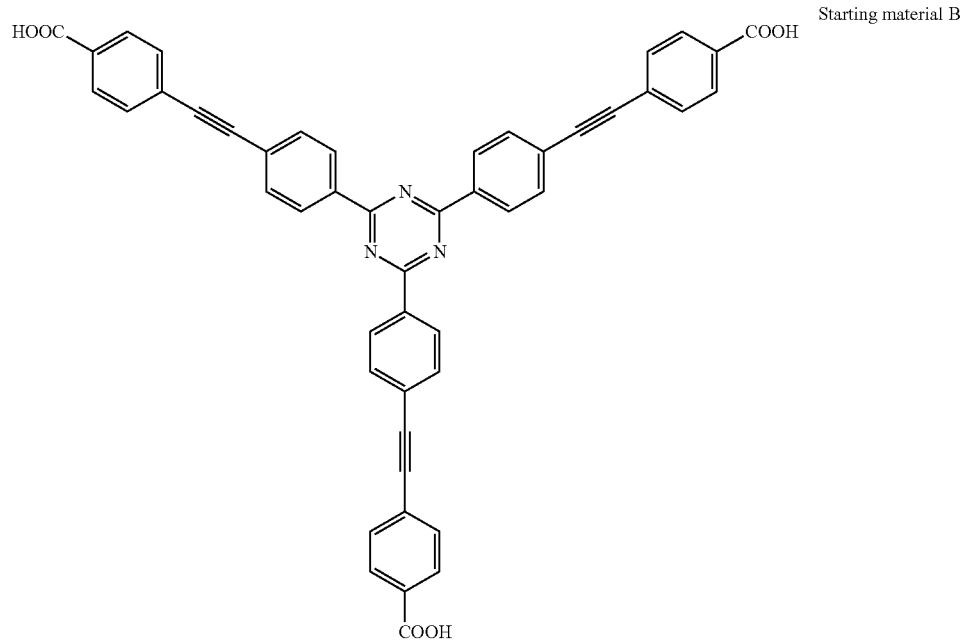

Starting material B

Figure 13:
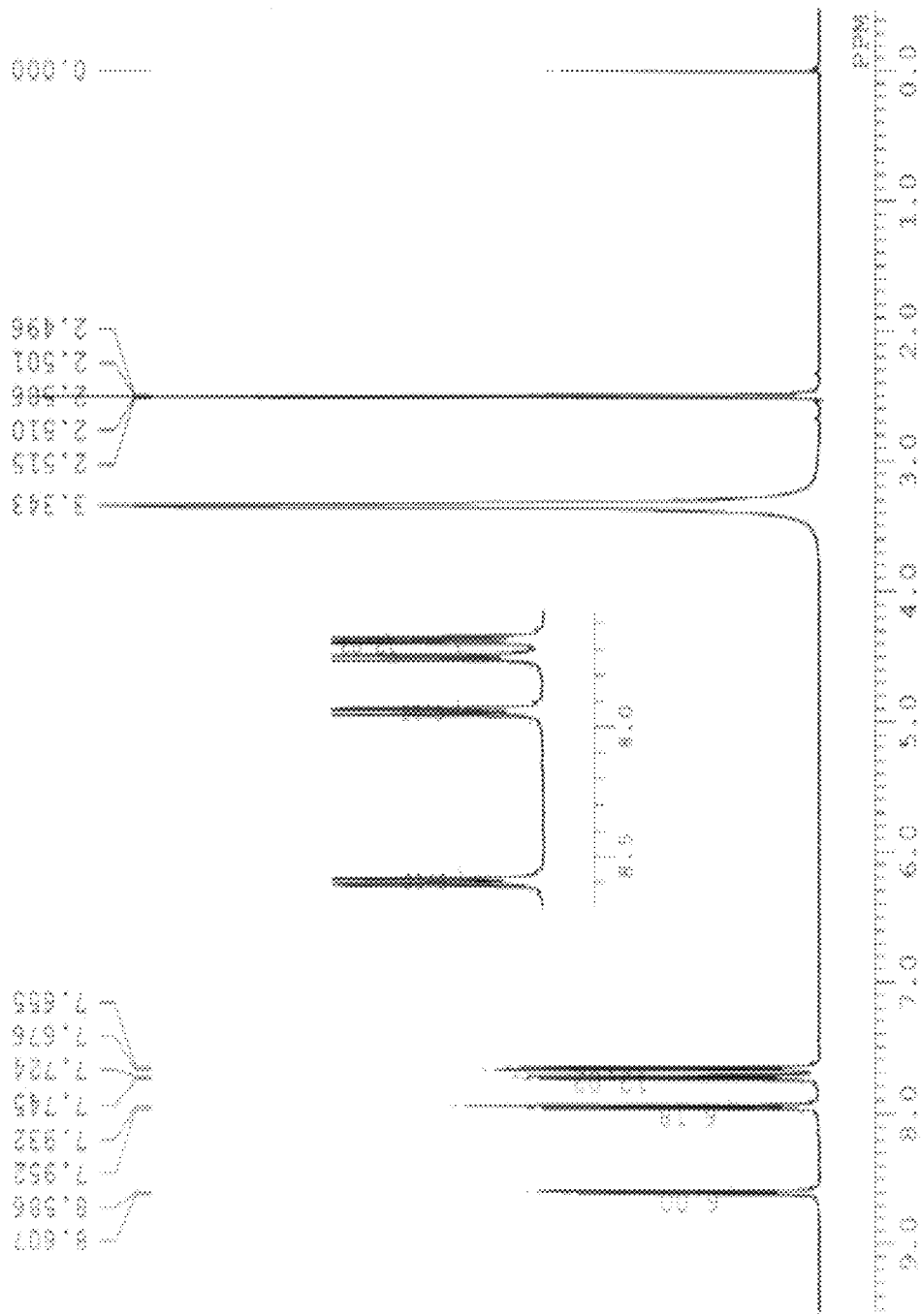
FIG. 13 shows an NMR spectrum of a tricarboxylic acid starting material B used in the inventive example 3.

FIG. 13 shows an NMR spectrum of the tricarboxylic acid starting material B.

Then, the mixture was stirred to provide a solution. After covering the glass tube with the lid, the solution was left at rest at 100 degrees Celsius for 72 hours. During this period of 72 hours, $Zn_4O^{6+}$ clusters were formed first, and then, a carboxyl group ion contained in the ligand B (i.e., a tricarboxylic acid ion) shown below was bound to the $Zn_4O^{6+}$ cluster. This coordinate bond was repeated, and a polymer which was finally formed three-dimensionally was precipitated as the porous coordination polymer PMOF-1N.

[Chem. 16]

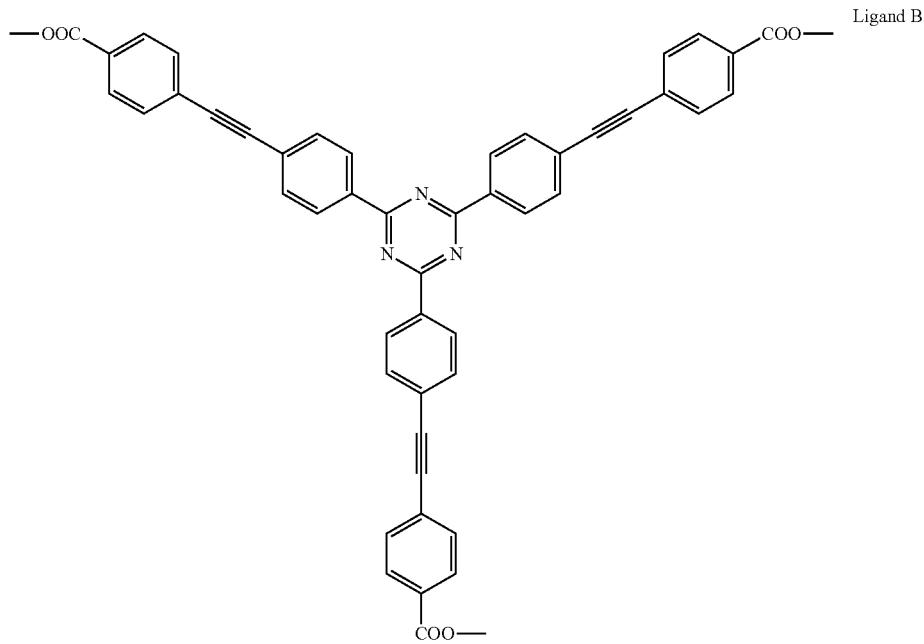

Ligand B

Then, the porous coordination polymer PMOF-1N was purified similarly to the case of the inventive example 1.

(Identification of the Structure of the Porous Coordination Polymer PMOF-1N)

Figure 14:
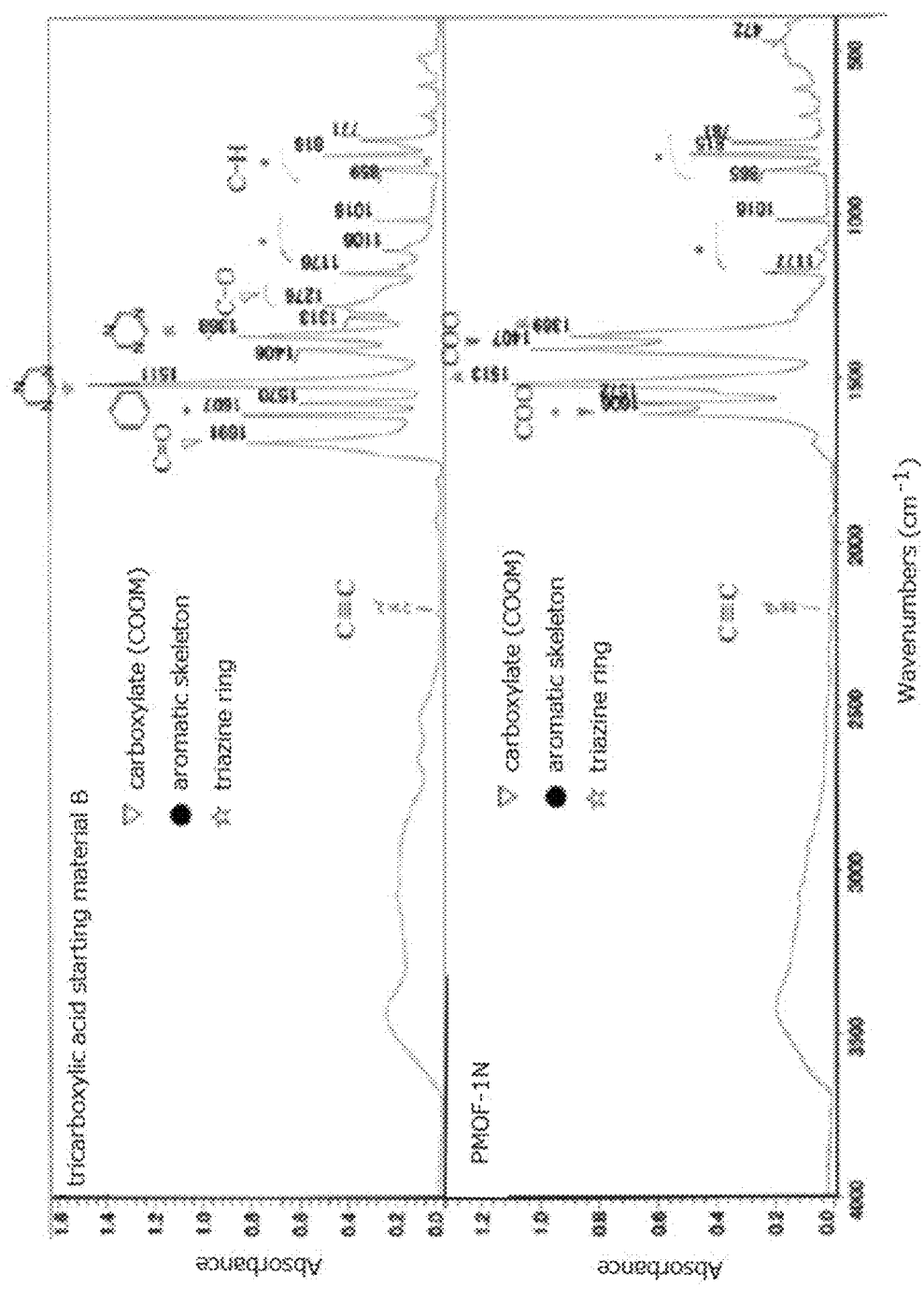
FIG. 14 shows an IR spectrum of the porous coordination polymer PMOF-1N synthesized in the inventive example 3 and an IR spectrum of the tricarboxylic acid starting material B used in the inventive example 3.
Figure 15:
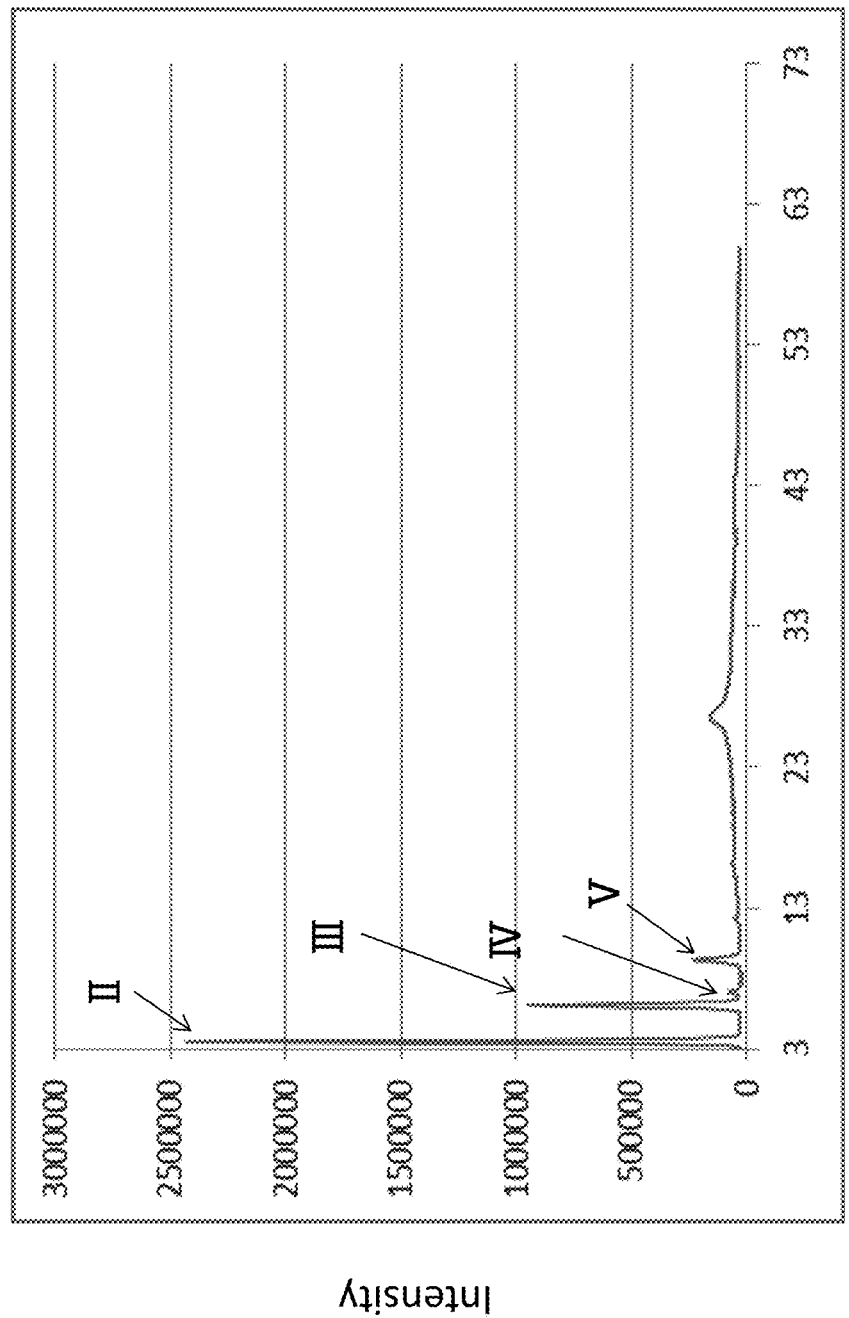
FIG. 15 shows an XRD spectrum of the porous coordination polymer PMOF-1N synthesized actually in the inventive example 3.

The above-provided porous coordination polymer PMOF-1N was subjected to an X-ray diffraction analysis. FIG. 15 shows an XRD spectrum of the porous coordination polymer PMOF-1N. Furthermore, the porous coordination polymer PMOF-1N was also subjected to an infrared spectroscopic analysis. FIG. 14 shows an IR spectrum of the porous coordination polymer PMOF-1N and an IR spectrum of the tricarboxylic acid starting material B.

Similarly to the case of the inventive example 1, the present inventors compared the actual peaks included in the XRD spectrum of the porous coordination polymer PMOF-1N with the predicted peaks of the XRD spectrum predicted on the basis of the structure of the porous coordination polymer MOF-177.

The radius $r_{12B}$ of the terdentate ligand 12 contained in the porous coordination polymer PMOF-1N was 1.568 nanometers on the basis of the calculation with reference to Table 1.

Figure 16:
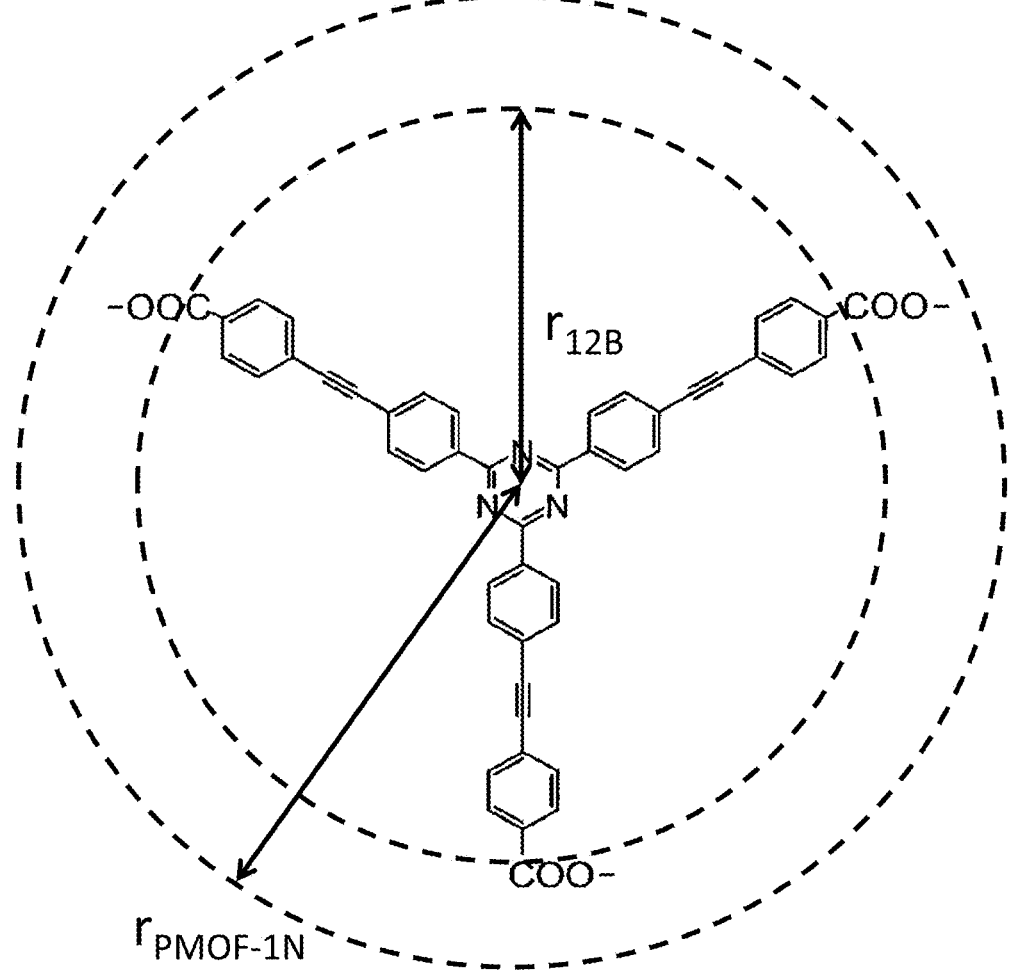
FIG. 16 shows a schematic view of the structure of the porous coordination polymer PMOF-1N under presumption that the porous coordination polymer PMOF-1N has the same structure as the porous coordination polymer MOF-177.

The radius $r_{PMOF-1N}$ of the porous coordination polymer PMOF-1N (namely, the distance between the center and the periphery of the porous coordination polymer PMOF-1N including the $Zn_4O^{6+}$ clusters) was 1.765 nanometers on the basis of the calculation with reference to Table 1. The radius $r_{PMOF-1N}$ indicated in FIG. 16 is equal to a half of the case size (See FIG. 1) in the inventive example 3.

Under presumption that the porous coordination polymer PMOF-1N has the same structure as the porous coordination polymer MOF-177 and that both of the porous coordination polymers have the same XRD spectrum shape as each other, the present inventors calculated the 2θ values at which the predicted peaks appear in the XRD spectrum of the porous coordination polymer PMOF-1N on the basis of the following three values as below.

(Value (i)): Radius $r_{MOF-177}$ (namely, 1.06 nanometers)

(Value (ii)): Radius $r_{PMOF-1N}$ (namely, 1.765 nanometers)

(Value (iii)): 2θ values at which the peaks appear in the XRD spectrum of the porous coordination polymer MOF-177 (see FIG. 5A).

FIG. 16 shows a schematic view of the structure of the porous coordination polymer PMOF-1N under presumption that the porous coordination polymer PMOF-1N has the same structure as the porous coordination polymer MOF-177.

Since the mathematical formula "$n\lambda=2d\cdot\sin\theta$" is satisfied on the basis of the Bragg's law, the following mathematical formula (IV3) is satisfied.

$$2k(1.06 \text{ nanometers})\cdot\sin\theta_1 = 2k(1.765 \text{ nanometers})\cdot\sin\theta_2 \quad \text{(IV3)}$$

where $\theta_1$ represents a diffraction angle of the porous coordination polymer MOF-177, $\theta_2$ represents a diffraction angle of the porous coordination polymer PMOF-1N, and k represents an integer.

The following mathematical formula (V3) is satisfied on the basis of the mathematical formula (IV3).

$$\sin\theta_2 = 1.06(\sin\theta_1)/1.765 \quad \text{(V3)}$$

Since the value of $2\theta_1$ is equal to 5.2° at the peak A included in FIG. 5A, the following mathematical formula (VI3) is satisfied on the basis of the mathematical formula (V3).

$$\sin \theta_2 = 1.06(\sin(5.2/2))/1.765 \quad (VI3)$$

Therefore, the value $2\theta_2$ is equal to 3.1°.

Likewise, at the peaks B, C, D, and E included in FIG. 5A, the $2\theta_1$ values are equal to 6.9°, 10.9°, 13.2°, and 18.0°. Therefore, on the basis of the mathematical formula (V3), the four mathematical formulas $2\theta_2=4.1°$, $2\theta_2=6.5°$, $2\theta_2=7.9°$, and $2\theta_2=10.8°$ are satisfied.

FIG. 15 shows an XRD spectrum of the porous coordination polymer PMOF-1N synthesized actually in the inventive example 3. The above-predicted five $2\theta_2$ values accord substantially with the 2θ values of the peaks II, III, IV, and V included in the XRD spectrum of the porous coordination polymer PMOF-1N synthesized actually in the inventive example 3. In FIG. 15, the peak I which corresponds to the $2\theta_2$ value of 3.1° does not appear. This is due to measurement limit of the XRD spectrum measurement device. This does not mean that the peak I which corresponds to the peak A did not appear.

As is clear from the comparison of FIG. 15 with FIG. 5A, the $2\theta_2$ values of the peaks II, III, IV, and V of the porous coordination polymer PMOF-1N are smaller than the $2\theta_1$ values of the peaks B, C, D, and E of the porous coordination polymer MOF-177, respectively. This means that the pore size and the cage size of the porous coordination polymer PMOF-1N is larger than those of the porous coordination polymer MOF-177.

As shown in FIG. 14, in the IR spectrum of the porous coordination polymer PMOF-1N, the peaks of the carboxyl acid included in the starting material B was changed to the peaks of the carboxylate.

On the basis of the above results, the present inventors believe that the porous coordination polymer PMOF-1N has the same structure as the porous coordination polymer MOF-177.

(Ability of Storing Hydrogen Molecules of the Porous Coordination Polymer PMOF-1N)

Similarly to the case of the inventive example 1, the ability of storing hydrogen molecules of the porous coordination polymer PMOF-1N (100 mg) provided in the inventive example 3 was evaluated.

Figure 17:
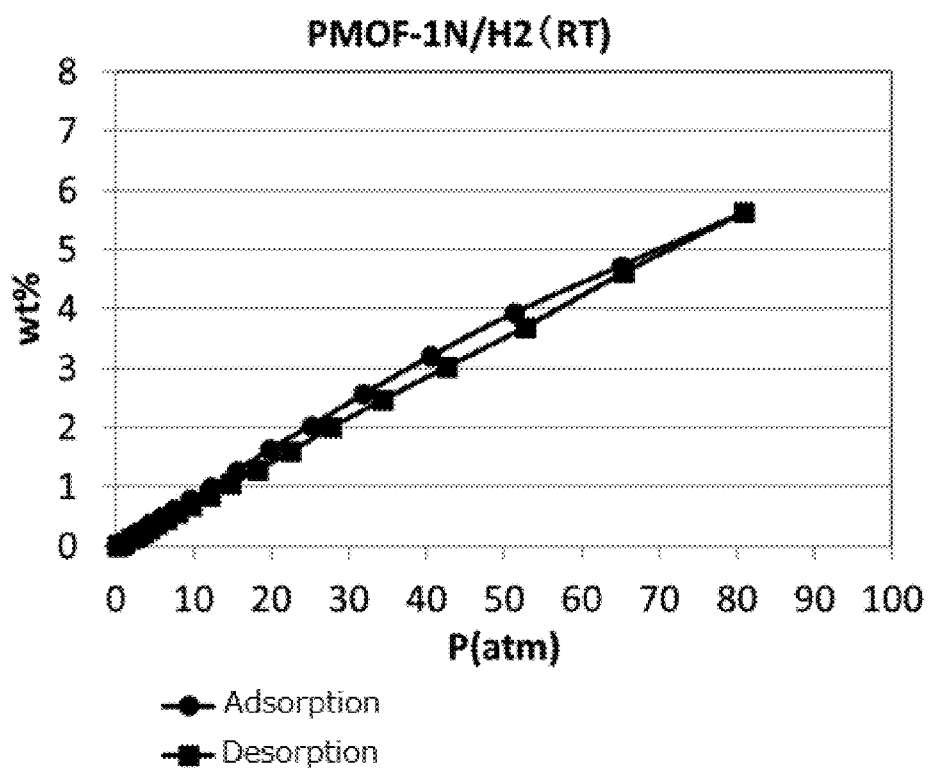
FIG. 17 is a graph showing the results of the hydrogen adsorption-desorption experience of the porous coordination polymer PMOF-1N synthesized in the inventive example 3.

FIG. 17 shows a graph showing the results of this experiment. As is clear from FIG. 17, the porous coordination polymer PMOF-1N has high ability of hydrogen adsorption-desorption.

Inventive Example 4

(Synthesis of the Porous Coordination Polymer PMOF-3)

In the inventive example 4, the porous coordination polymer PMOF-3 represented by the chemical formula (III) in which the value of X is equal to 1 was synthesized as below.

The following three reagents were added to a glass tube having a capacity of 30 mL to provide a mixture.

| | |
|---|---|
| N,N-dimethylformamide | 20 milliliters (purchased from Wako Pure Chemical Industries, Ltd., infinity pure grade) |
| Zinc nitrate terahydrates | 0.5 grams (purchased from Merck KGaA) |
| Tricarboxylic acid starting material C | 0.5 grams (purchased from Nard Institute, ltd.) |

[Chem. 19]

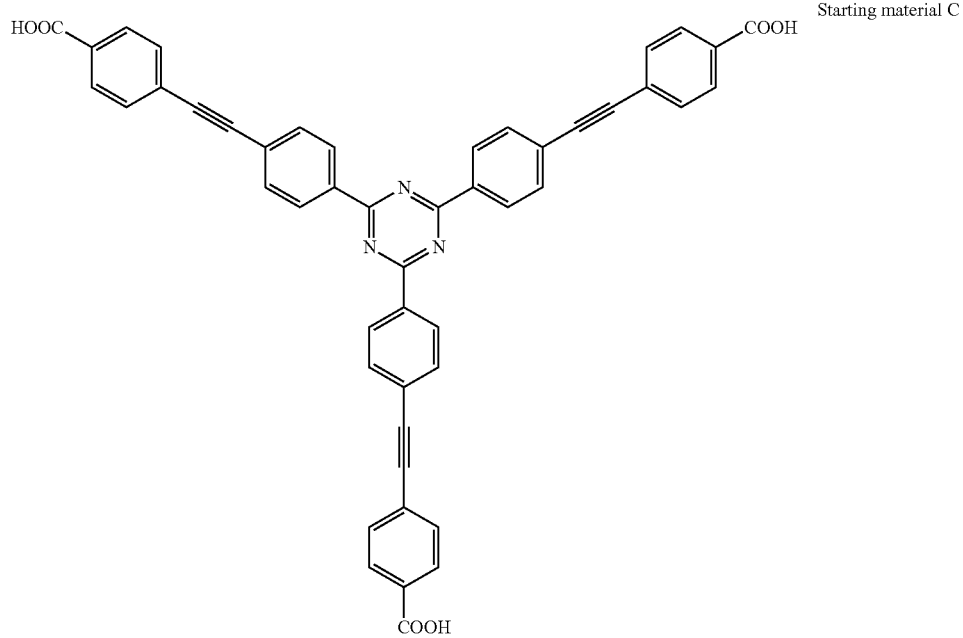

Starting material C

Figure 18:
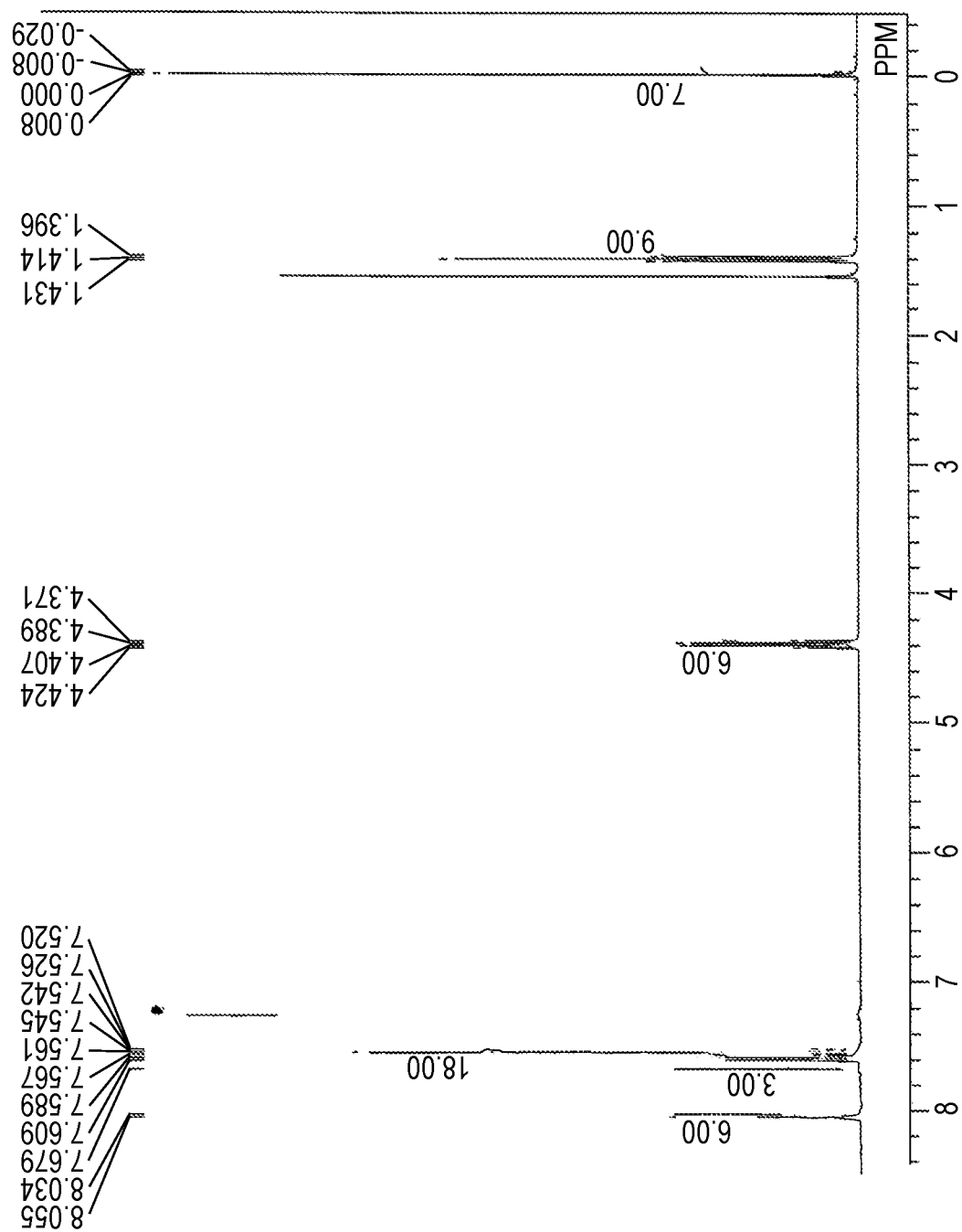
FIG. 18 shows an NMR spectrum of a tricarboxylic acid starting material C used in the inventive example 4.

FIG. 18 shows an NMR spectrum of the tricarboxylic acid starting material C.

Then, the mixture was stirred to provide a solution. After covering the glass tube with the lid, the solution was left at rest at 100 degrees Celsius for 72 hours. During this period of 72 hours, $Zn_4O^{6+}$ clusters were formed first, and then, a carboxyl group ion included in the ligand C (i.e., a tricarboxylic acid ion) shown below was bound to the $Zn_4O^{6+}$ cluster. This coordinate bond was repeated, and a polymer which was finally formed three-dimensionally was precipitated as the porous coordination polymer PMOF-3.

[Chem. 20]

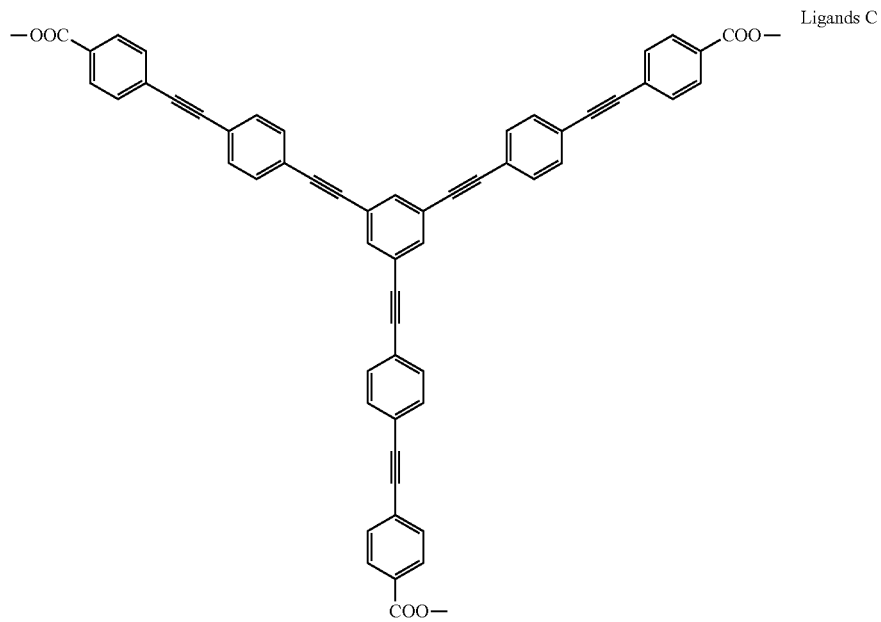

Ligands C

Then, the porous coordination polymer PMOF-3 was purified similarly to the case of the inventive example 1.

(Identification of the Structure of the Porous Coordination Polymer PMOF-3)

Figure 19:
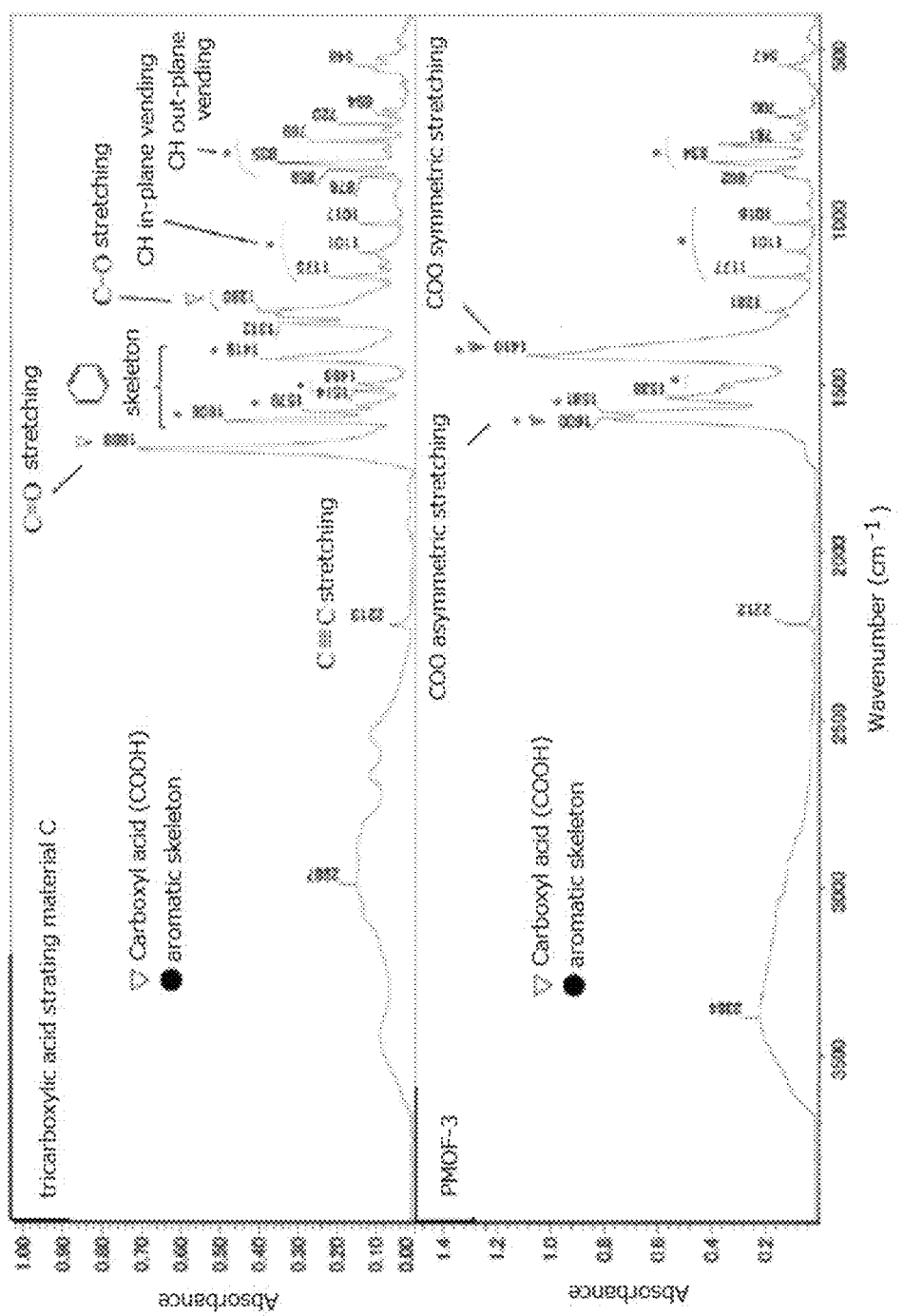
FIG. 19 shows an IR spectrum of the porous coordination polymer PMOF-3 synthesized in the inventive example 4 and an IR spectrum of the tricarboxylic acid starting material C used in the inventive example 4.
Figure 20:
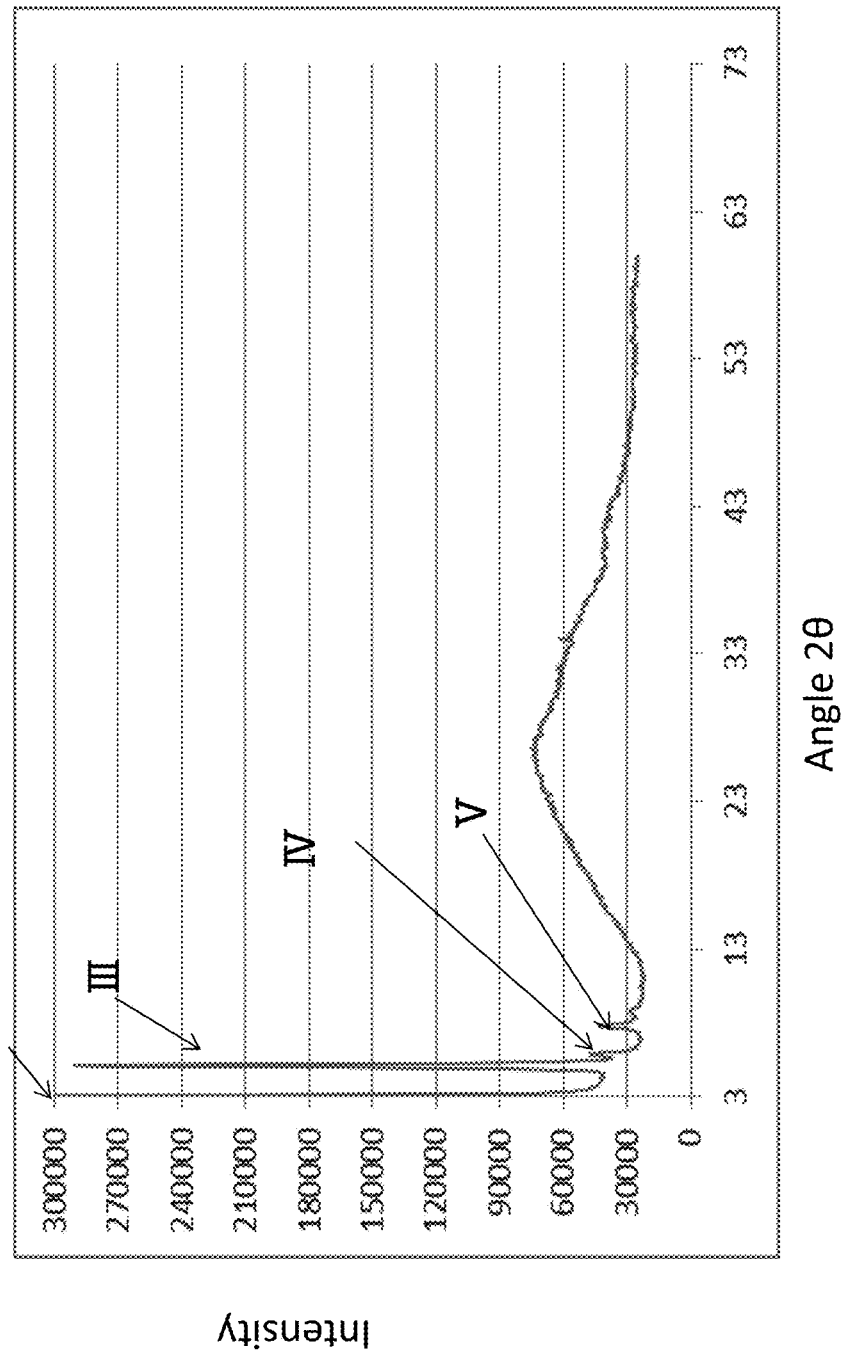
FIG. 20 shows an XRD spectrum of the porous coordination polymer PMOF-3 synthesized actually in the inventive example 4.

The above-provided porous coordination polymer PMOF-3 was subjected to an X-ray diffraction analysis. FIG. 20 shows an XRD spectrum of the porous coordination polymer PMOF-3. Furthermore, the porous coordination polymer PMOF-3 was also subjected to an infrared spectroscopic analysis. FIG. 19 shows an IR spectrum of the porous coordination polymer PMOF-3 and an IR spectrum of the tricarboxylic acid starting material C.

Similarly to the case of the inventive example 1, the present inventors compared the actual peaks included in the XRD spectrum of the porous coordination polymer PMOF-3 with the predicted peaks of the XRD spectrum predicted on the basis of the structure of the porous coordination polymer MOF-177.

The radius $r_{12C}$ of the terdentate ligand 12 included in the porous coordination polymer PMOF-3 was 1.840 nanometers on the basis of the calculation with reference to Table 1.

Figure 21:
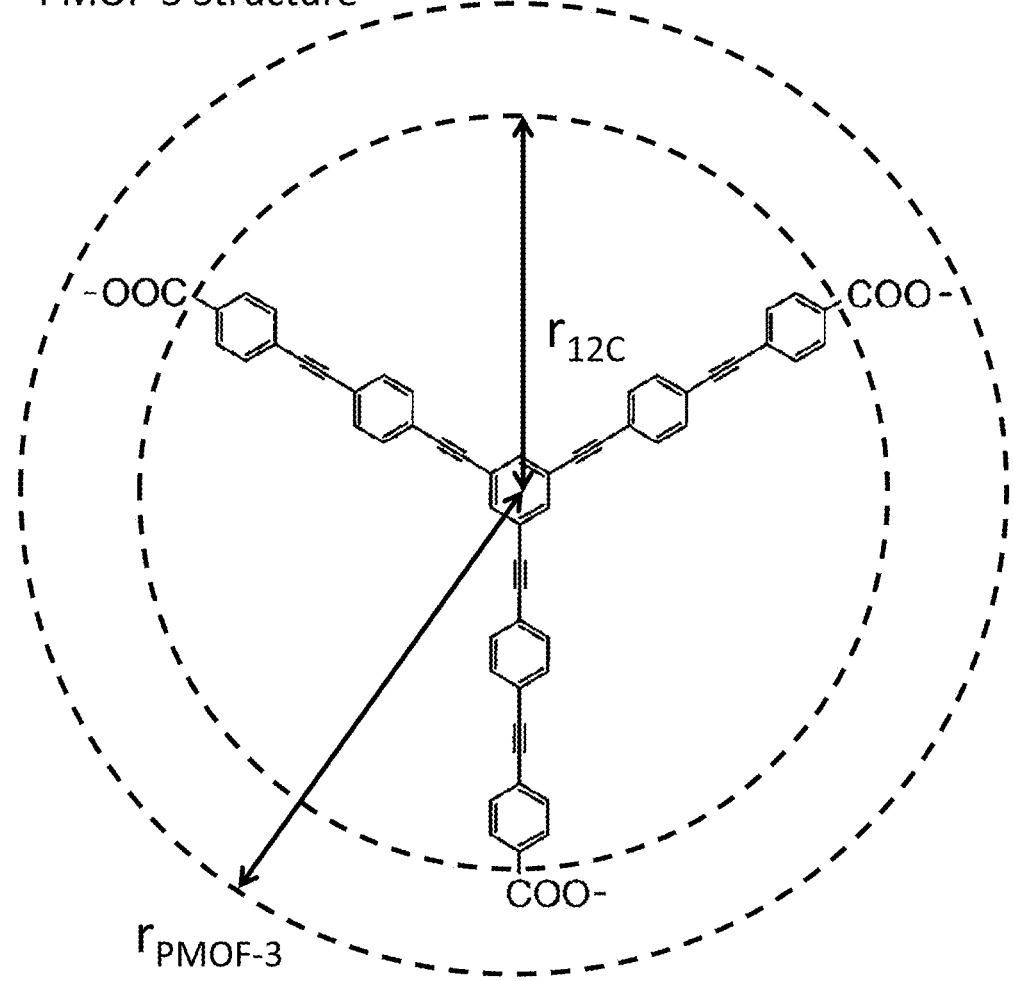
FIG. 21 shows a schematic view of the structure of the porous coordination polymer PMOF-3 under presumption that the porous coordination polymer PMOF-3 has the same structure as the porous coordination polymer MOF-177.

The radius $r_{PMOF-3}$ of the porous coordination polymer PMOF-3 (namely, the distance between the center and the periphery of the porous coordination polymer PMOF-3 including the $Zn_4O^{6+}$ clusters) was 2.037 nanometers on the basis of the calculation with reference to Table 1. The radius $r_{PMOF-3}$ indicated in FIG. 21 is equal to a half of the case size (See FIG. 1) in the inventive example 4.

Under presumption that the porous coordination polymer PMOF-3 has the same structure as the porous coordination polymer MOF-177 and that both of the porous coordination polymers have the same XRD spectrum shape as each other, the present inventors calculated the 2θ values at which the predicted peaks appear in the XRD spectrum of the porous coordination polymer PMOF-3 on the basis of the following three values as below.

(Value (i)): Radius $r_{MOF-177}$ (namely, 1.06 nanometers)

(Value (ii)): Radius $r_{PMOF-3}$ (namely, 2.037 nanometers)

(Value (iii)): 2θ values at which the peaks appear in the XRD spectrum of the porous coordination polymer MOF-177 (see FIG. 5A).

FIG. 21 shows a schematic view of the structure of the porous coordination polymer PMOF-3 under presumption that the porous coordination polymer PMOF-3 has the same structure as the porous coordination polymer MOF-177.

Since the mathematical formula "$n\lambda = 2d \cdot \sin \theta$" is satisfied on the basis of the Bragg's law, the following mathematical formula (IV4) is satisfied.

$$2k(1.06 \text{ nanometers}) \cdot \sin \theta_1 = 2k(2.037 \text{ nanometers}) \cdot \sin \theta_2 \quad \text{(IV4)}$$

where $\theta_1$ represents a diffraction angle of the porous coordination polymer MOF-177, $\theta_2$ represents a diffraction angle of the porous coordination polymer PMOF-3, and k represents an integer.

The following mathematical formula (V4) is satisfied on the basis of the mathematical formula (IV4).

$$\sin \theta_2 = 1.06(\sin \theta_1)/2.037 \quad \text{(V4)}$$

Since the value of $2\theta_1$ is equal to 5.2° at the peak A included in FIG. 5A, the following mathematical formula (VI4) is satisfied on the basis of the mathematical formula (V4).

$$\sin\theta_2 = 1.06(\sin(5.2/2))/2.037 \quad (VI4)$$

Therefore, the value $2\theta_2$ is equal to 2.7°.

Likewise, at the peaks B, C, D, and E included in FIG. 5A, the $2\theta_1$ values are equal to 6.9°, 10.9°, 13.2°, and 18.0°. Therefore, on the basis of the mathematical formula (V4), the four mathematical formulas $2\theta_2=3.6°$, $2\theta_2=5.7°$, $2\theta_2=6.9°$, and $2\theta_2=9.3°$ are satisfied.

FIG. 20 shows an XRD spectrum of the porous coordination polymer PMOF-3 synthesized actually in the inventive example 4. The above-predicted five $2\theta_2$ values accord substantially with the $2\theta$ values of the peaks II, III, IV, and V included in the XRD spectrum of the porous coordination polymer PMOF-3 synthesized actually in the inventive example 4. In FIG. 20, the peak I which corresponds to the $2\theta$ value of 3.1° does not appear. This is due to measurement limit of the XRD spectrum measurement device. This does not mean that the peak I which corresponds to the peak A did not appear.

As is clear from the comparison of FIG. 20 with FIG. 5A, the $2\theta_2$ values of the peaks II, III, IV, and V of the porous coordination polymer PMOF-3 are smaller than the $2\theta_1$ values of the peaks B, C, D, and E of the porous coordination polymer MOF-177, respectively. This means that the pore size and the cage size of the porous coordination polymer PMOF-3 is larger than those of the porous coordination polymer MOF-177.

As shown in FIG. 19, in the IR spectrum of the porous coordination polymer PMOF-3, the peaks of the carboxyl acid included in the starting material C was changed to the peaks of the carboxylate.

On the basis of the above results, the present inventors believe that the porous coordination polymer PMOF-3 has the same structure as the porous coordination polymer MOF-177.

(Ability of Storing Hydrogen Molecules of the Porous Coordination Polymer PMOF-3)

Similarly to the case of the inventive example 1, the ability of storing hydrogen molecules of the porous coordination polymer PMOF-3 (100 mg) provided in the inventive example 4 was evaluated.

Figure 22:
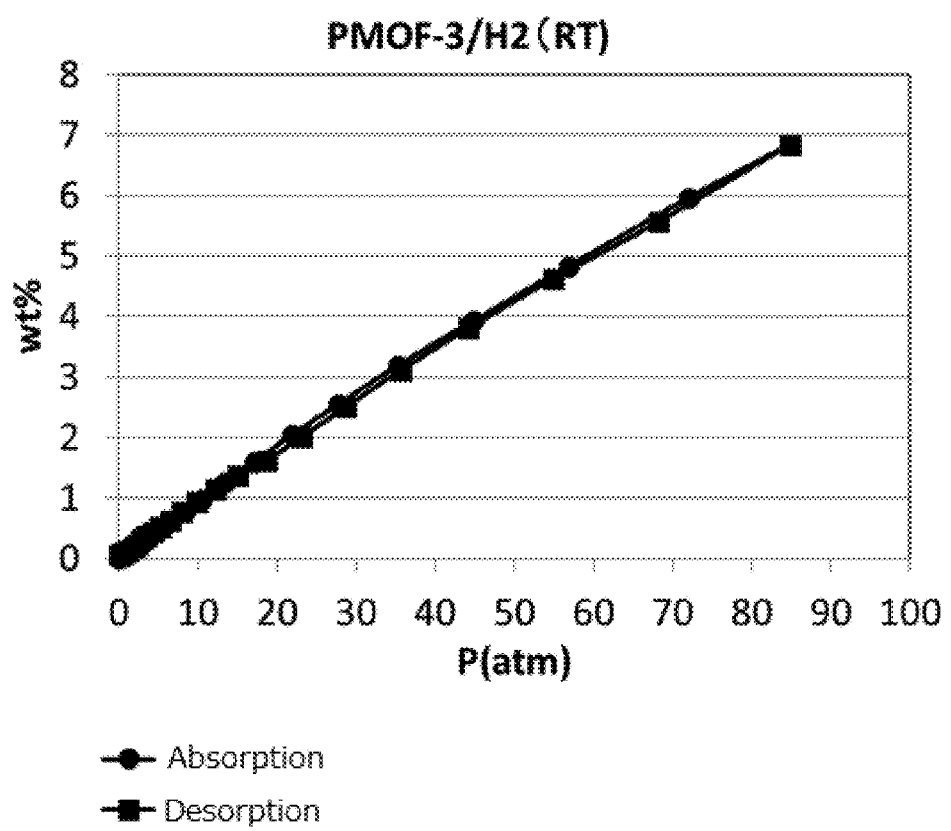
FIG. 22 is a graph showing the results of the hydrogen adsorption-desorption experience of the porous coordination polymer PMOF-3 synthesized in the inventive example 4.

FIG. 22 shows a graph showing the results of this experiment. As is clear from FIG. 22, the porous coordination polymer PMOF-3 has high ability of hydrogen adsorption-desorption.

Comparative Example 1

(Synthesis of the Porous Coordination Polymer MOF-177)

In the comparative example 1, the porous coordination polymer MOF-177 represented by the chemical formula (I) in which the value of x is equal to 0 was synthesized. The porous coordination polymer MOF-177 was synthesized similarly to the porous coordination polymer PMOF-1 according to the inventive example 1, except for using 1,3,5-tris(4-carboxyphenyl) benzene (CAS No.: 50446-44-1) in place of the starting material A1.

(Ability of Storing Hydrogen Molecules of the Porous Coordination Polymer MOF-177)

Similarly to the case of the inventive example 1, the ability of storing hydrogen molecules of the porous coordination polymer MOF-177 (100 mg) provided in the comparative example 1 was evaluated.

Figure 23:
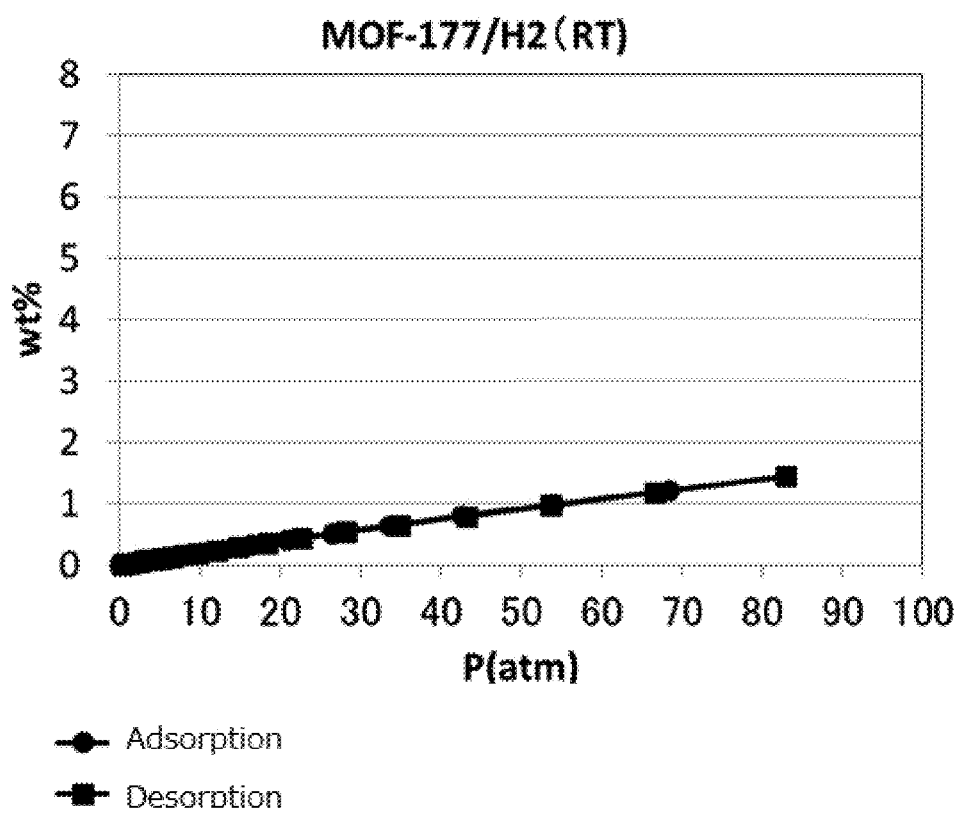
FIG. 23 is a graph showing the results of the hydrogen adsorption-desorption experience of the porous coordination polymer MOF-177 used in the comparative example 1.

FIG. 23 shows a graph showing the results of this experiment. As is clear from the comparison of FIG. 7, FIG. 12, FIG. 17, and FIG. 22 with FIG. 23, the porous coordination polymer PMOF-177 has much lower ability of hydrogen adsorption-desorption than the porous coordination polymers PMOF-1, PMOF-5, PMOF-1N, and PMOF-3.

INDUSTRIAL APPLICABILITY

For example, the porous coordination polymer according to the present disclosure can be used for a fuel cell.

REFERENTIAL SIGNS LIST

1 Porous coordination polymer
11 $Zn_4O^{6+}$ cluster
12 Terdentate ligand
2 Hydrogen storing device
21 Sealed container
22 Inlet
23 Valve
24 Thermostat bath

The invention claimed is:
1. A porous coordination polymer comprising:
zinc cluster ions; and
one kind of tricarboxylic acid ions selected from the group consisting of the following chemical formula (I) and the following chemical formula (II);

[Chem. 1]

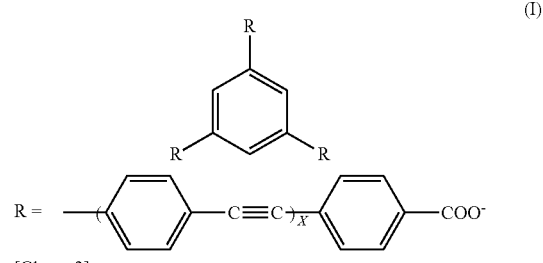

(I)

[Chem. 2]

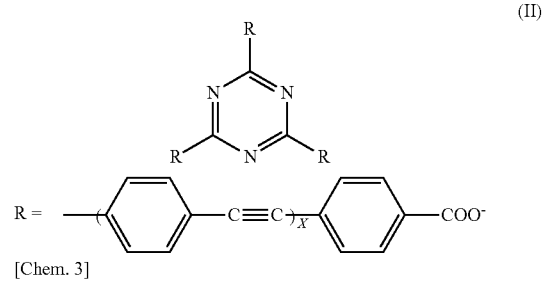

(II)

[Chem. 3]

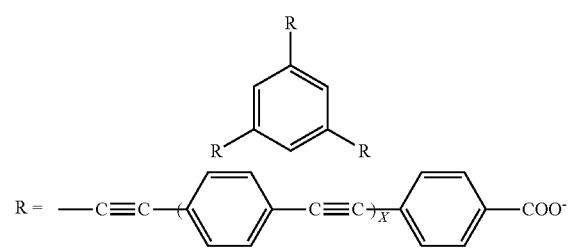

(III)

where X represents a natural number of not less than 1 and not more than 3, wherein the tricarboxylic acid ions are bound to the zinc cluster ions as terdentate ligands.

2. The porous coordination polymer according to claim 1, wherein the tricarboxylic acid is selected from the chemical formula (I).

3. The porous coordination polymer according to claim 1, wherein the tricarboxylic acid is selected from the chemical formula (II).

4. The porous coordination polymer according to claim 1, wherein the value of x is not less than 1 and not more than 2.

5. A method for storing a gas, the method comprising:

(a) bringing the gas into contact with a porous coordination polymer to store the gas in the porous coordination polymer;

wherein the porous coordination polymer is a porous coordination polymer according to claim 1.

6. The method according to claim 5, wherein the gas is at least one selected from a hydrogen gas and a hydrocarbon gas.

7. The method according to claim 5, wherein the tricarboxylic acid is selected from the chemical formula (I).

8. The method according to claim 5, wherein the tricarboxylic acid is selected from the chemical formula (II).

9. The method according to claim 5, wherein the value of x is not less than 1 and not more than 2.

10. The method according to claim 6, wherein the gas is selected from the hydrogen gas.

11. The method according to claim 5, wherein the gas is brought into contact with the porous coordination polymer at a temperature of not less than 0 degree Celsius and not more than 50 degrees Celsius.

12. A gas storage device, comprising:

a sealed container; and a porous coordination polymer according to claim 1, wherein the porous coordination polymer is disposed in the sealed container.

13. The gas storage device according to claim 12, wherein the sealed container comprises an inlet.

* * * * *